United States Patent [19]

Ambesi-Impiombato

[11] Patent Number: 4,608,341
[45] Date of Patent: Aug. 26, 1986

[54] LIVING, FAST-GROWING THYROID CELL STRAIN, FRTL-5

[75] Inventor: Francesco S. Ambesi-Impiombato, Naples, Italy

[73] Assignee: Interthyr Research Foundation, Inc., Md.

[21] Appl. No.: 499,250

[22] Filed: May 31, 1983

[51] Int. Cl.[4] .................. C12N 5/00; C12R 1/91
[52] U.S. Cl. .................................. 435/240; 435/948
[58] Field of Search ............... 435/240, 241, 948, 244

[56] References Cited

PUBLICATIONS

Laccetti et al, "Ganglioside Dependent Return of TSH Receptor Function in a Rat Thyroid with a TSH Receptor Defect," Biochemical and Biophysical Research Communications 110(3) pp. 772–778, (1983).
Beguinot et al, "Structural Changes Caused by Thyrotropin in Thyroid Cells and in Liposomes Containing Reconstituted . . . " Biochemical and Biophysical Research Communications 110(1) pp. 48–54, (1983).
Avivi et al, "Adenosine 3′, 5′—Monophosphate Modulated Thyrotropin Receptor Clustering and Thyrotropin Activity in Culture, " Science 214, p. 1237, (1981).
Ambesi—Impiombato, "Influence of Hormones and Serum on Growth and Differentiation of the Thyroid Cell Strain FRTL," Growth of Cells in Hormonally Defined Media, ed. Sato et al, Cold Spring Harbor Laboratory, 1982, pp. 483–492.
"Culture of Hormone—Dependent Epithelial Cells From Rat Thyroids", Proceedings of the National Academy of Science USA, 77: 3455–3459, (1980), F. S. Ambesi—Impiombato, L. A. M. Parks and H. G. Coon.

Primary Examiner—Blondel Hazel
Assistant Examiner—John Edward Tarcza
Attorney, Agent, or Firm—Leydig, Voit & Mayer, Ltd.

[57] ABSTRACT

A fast growing, continuous, functional rat thyroid cell strain, FRTL-5, which maintains functional characteristics of iodide uptake and thyroglobulin synthesis over prolonged periods of culture is cloned from FRTL cells obtained from primary cultures of Fischer rat thyroid glands. The FRTL-5 cells are cultured in a medium containing approximately 5 percent calf serum supplemented with a mixture of hormones, at least one of which is thyrotropin.

The FRTL-5 cells are employed in a series of assays which measure thyroid stimulatory or inhibitory factors. The FRTL-5 system of assay specifically measures thymidine incorporation, cAMP elevation and iodide uptake and permits the evaluation of patient sera, particularly those afflicted with Graves' disease and other autoimmune thyroid diseases, thereby providing a means for determining appropriate methods of treatment.

10 Claims, 18 Drawing Figures

LIVING, FAST-GROWING THYROID CELL STRAIN, FRTL-5

TECHNICAL FIELD

The present invention relates to a living, fast-growing thyroid cell strain. More particularly, the present invention relates to a cloned normal rat thyroid cell strain, FRTL-5, derived from FRTL cells, which cell strain maintains all normal thyroid cell functions, including hormonal responsiveness, iodide uptake and thyroglobulin synthesis over prolonged periods of culture.

The present invention also relates to clinical assays of thyrotropin and a variety of thyroid stimulatory or inhibitory factors. More specifically, this aspect of the invention permits the in vitro determination and/or quantification of human autoantibodies which modulate (a) excess growth, (b) cAMP (cyclic adenosine monophosphate) and (c) iodide uptake.

BACKGROUND ART

The differentiated function of the thyroid cell is regulated in large measure by thyrotropin, also known as thyroid stimulating hormone (TSH). Receptormediated effects of TSH on adenylate cyclase activity, with eventual regulation of iodoprotein metabolism, are generally accepted. Receptor-mediated effects of TSH on electrochemical ion gradients independent of the effect of TSH on adenylate cyclase activity have also been demonstrated although the role of this phenomenon in the differentiation or function of the cell is not clear. Finally, TSH is known to have a trophic effect on thyroid cells. Thus, numerous studies have shown that the growth of functioning thyroid cells is accelerated by, or absolutely requires, the presence of TSH.

Graves' disease, an autoimmune thyroid disease characterized by primary hyperthyroidism, is sometimes indicated by the presence of a goiter. It was originally thought that Graves' disease was related to high blood levels of thyrotropin (TSH). Subsequent studies of blood samples taken from patients afflicted with Graves' disease indicated that TSH could not usually be found at elevated levels. The failure to detect small amounts of TSH may be due, in part, to the methods of assay used therefor. Thus, the radioimmunoassay technique which has been used for decades and continues to be in current use depends upon measurement of iodinated TSH in a displacement test; it does not measure bioactive TSH, but rather immunologically reactive TSH, i.e., TSH which reacts with an antibody directed at a number of its structural features rather than only those features important for bioactivity or function. This technique, which is dependent upon a very potent anti-TSH antibody, the iodinated label in TSH, the purity of the labeled TSH and the quality of the antibody, is also incapable of detecting low levels of TSH since, at best, the limits of assay sensitivity are only in the range of normal serum TSH levels.

Still other studies indicated that Graves' disease was associated with autoantibodies in the circulation which were capable of stimulating thyroid function. Two types of stimulating autoantibodies are now known, those that mimic the TSH regulatory controls over growth and those that mimic the regulatory control over adenylate cyclase activity (cAMP levels). In other autoimmune thyroid diseases, autoantibody thyroid factors which inhibit as well as stimulate thyroid function are postulated. In each case the prior history of the thyroid preparation, for example, specific patient characteristics or prior therapy, might well influence the particular autoimmune antibody or TSH response elicited.

The first assay method for Graves' disease immunoglobulins (GD IgGs) found in patient sera was known as long acting thyroid stimulator (LATS) assay. LATS is measured by an in vivo assay which involves administering the immunoglobulin fraction of the patient to a mouse whose thyroid has been injected with radioiodide. The presence of certain immunoglobulins causes a release of thyroid hormones from the radioiodinated mouse gland. The shortcomings of the LATS assay primarily are that it is capable of giving positive results in only 40 to 50 percent of cases in which it is used; it does not measure a significant number of stimulators detected by measurement of immunoglobulin-enhanced adenylate cyclase activity in human membrane, slice or cell preparations; it requires approximately four to eight mice per single dose of IgG sample and as many as twenty-four for a full dose curve, each mouse requiring 1 to 2 weeks of preparation time and 1 day of assay time, and its activity does not correlate with the severity or extent of the clinical disease. The drawback that the LATS assay was not sensitive to all thyroid stimulating immunoglobulins in a patient led to the measurements of stimulating antibodies in human membrane cell or slice systems. The assumption on which these assays are based was that the fundamental autoantibody stimulating activity was its ability to stimulate adenylate cyclase activity. The cyclic AMP thus produced appeared to function as a "second messenger" in the respect that it further stimulated the cell to perform many of its routine functions, such as iodide uptake, production of thyroglobulin, the conversion of thyroglobulin to thyroid hormones, and the release of thyroid hormones into the blood. The assumption that all stimulators, whether TSH or an autoimmune antibody or IgG, would behave like TSH in stimulating adenylate cyclase activity led to the development of in vitro assays of elevated cAMP levels as a measure of all thyroid stimulators.

In the search for an accurate in vitro assay method, several human thyroid membrane, cell and slice preparations and techniques have been developed which rely on the similar stimulatory effects of the immunoglobulins, as compared to TSH, to elevate the amount of cyclic adenosine 3', 5'-monophosphate or cyclic adenosine monophosphate (cyclic AMP or cAMP) in these tissue preparations. Although the human slice or cell preparations, both of which are currently being used in Graves' disease assays, are capable of indirectly measuring a significant number of stimulators by determinations of immunoglobulin-enhanced adenylate cyclase activity and are, therefore, more sensitive to and have a higher positive correlation with the disease state, these techniques also suffer from certain shortcomings. Thus, human thyroid material is either not readily available or is only episodically available in most clinical settings and is not usually normal human tissue. The human material, even when available, also has a high degree of variability in response, a problem which may relate to the individualistic history of each tissue source. The thyroid slice and primary cell culture systems of assay also depend, to a large extent, on the individual skills, experience and subjective judgment of the analyst performing the assay, for example, the analyst's subjective assessment of what is "good" human thyroid tissue. In membranes in particular, the level of hormone stimulatable adenylate cyclase, the enzyme which produces cAMP, is present in only small amounts. Thyroid slices in particular cannot be preserved in any manner and must be used in a fresh condition.

Although a technique has been developed whereby primary cell cultures may be frozen and tests subsequently performed on aliquots withdrawn from the frozen culture, there are still certain inherent disadvantages with the technique. Human thyroid cells do not grow in vitro and, therefore, the number of tests which may be performed is limited by the quantity of primary cells obtained and the above variability problems. Secondly, after the cells are dispersed, a waiting period of from two to four days is required before the cells may be employed in an assay. Another problem associated with the primary culture system is that thyroid cells are contaminated with fibroblasts or other cells which can respond to TSH or autoimmuneantibodies by yielding other agents or prostaglandins which can, in turn, stimulate the cAMP response in the thyroid cell. The relationship of this activity to autoimmune thyroid disease is not yet clear.

It became apparent to scientists and physicians that to further define molecular and regulatory mechanisms of thyroid physiology and pathology and to permit the development of a rapid, accurate and easily conducted clinical determination and/or quantification of thyrotropin and of thyroid stimulatory or inhibitory factors, an improved in vitro system would be needed. The ideal system would, preferably, be one that demonstrates the properties and characteristics of a normal and non-malignant cell, established in long-term or permanent cultures, which-could be maintained in a totally controlled or chemically defined environment and cloned to give rise to genetically homogeneous cell populations. Such cells would also possess unlimited growth capacity while maintaining the expression of the biochemical markers belonging to the differentiated cell type from which they originated. A primary requirement of the cell line or strain is that their growth rate be rapid enough so that large populations of cells could be raised and used in either large-scale experiments or numerous assays.

Early studies seemed to suggest that a cell line of epithelial cells derived from normal Fischer rat thyroid (FRT) cells offered promise in assays of TSH and immunoglobulins in Graves' disease. Although FRT cells are extremely sensitive to cholera toxin, the FRT line lacks differentiated thyroid functions, such as TSH stimulated thyroglobulin biosynthesis and iodide trapping as a result of a defective glycoprotein component of the TSH receptor. These cells thus appear to be non-functioning or de-differentiated in culture. The FRT cell strain was isolated initially in medium supplemented with 5 percent serum and TSH or dibutyryl cyclic AMP and was subsequently conditioned by culture on thyroid fibroblasts. At first they were able to produce thyroglobulin in primary cultures but after adaptation to growth in unconditioned medium lost the ability to concentrate iodide or to produce thyroglobulin. Epithelial FRT cells possess a TSH-stimulatable membrane adenylate cyclase and ADP ribosyltransferase activity which does indicate their thyroid origin.

Another thyroid cell line FRTL, reported widely in the literature, was isolated from primary cell suspensions obtained from the thyroid glands of NIH Fischer 344 inbred strain of rats. The FRTL cell line was isolated in medium supplemented with 0.5 percent calf serum and purified hormones. The FRTL cell line, purified by successive colonial isolations, was found to maintain highly differentiated features, such as secretion into the culture medium of physiological amounts of thyroglobulin and the concentration of iodide by 100-fold, after three years in continuous culture. They were observed to maintain the same biochemical and morphological characteristics which typify the primary cultures of the thyroid follicular cells immediately after their enzymatic release from the rat thyroid, (Ambesi-Impiombato et al, *Proceedings of the National Academy of Science (USA)*, 77, pages 3455 to 3459 (1980)). However, this thyroid cell line demonstrates only a limited growth potential in vitro, the population doubling time being approximately 5 to 7 days in Coon's modified Ham's F-12 medium supplemented with 0.1 to 0.5 percent calf serum and six hormones at 37 degrees C. Indeed, the fact that normal cells have only a limited growth potential in vitro has been generally accepted as a rule (Impress and Hayflick, "The Limited In Vitro Life Time Of Human Diploid Cell Stains", *Experimental Cell Research*, 37, pages 614 to 636 (1965)). Thus, growth and irreversible de-differentiation appeared to be absolutely linked to each other in vitro. This was heretofore believed to be due to intrinsic properties of the differentiated cells. Another characteristic of this line which limits its usefulness in testing the "acute" effects of the addition of TSH is that withdrawal of TSH for more than 24 hours from the hormone mixture in which the cells are grown results in detachment of the cells from the surface of the culture dishes in which they are grown and their subsequent progressive death. The FRTL cell line is also unable to achieve growth to confluency, the cells existing only as isolated sparse cells. Finally, unlike the FRTL-5 strain, the FRTL cell line requires insulin as an absolute growth requirement.

DISCLOSURE OF THE INVENTION

The FRTL-5 cell strain which is employed in the assay methods of the present invention, described in greater detail below, is a cloned normal rat thyroid differentiated phenotype derived from FRTL cells which maintain functional characteristics of iodide uptake and thyroglobulin synthesis over prolonged periods of culture, on the order of two years. This differentiated cell strain, which has been deposited in the American Type Culture Collection and has an accession number of ATCC CRL 8305, exhibits a TSH-responsive adenylate cyclase, ion flux and phospholipid metabolic shift as well as an absolute growth requirement for TSH.

This cell strain is a continuously growing, well characterized, normal and differentiated phenotype having a diploid karyotype. This cell strain exhibits, in terms of normality, a diploid chromosome number, a lack of growth in semi-solid media or in syngeneic animals, contact inhibition, and a normal morphology of the chromosomes. In addition, it may be noted that the chromosome stability is rather high even though the FRTL-5 strain undergoes more than 250 cell generations per year. Differentiation, a characteristic of thyroid cells upon which the discriminating nature of the immunoassays of the present invention depend, may be defined by the parameters of iodide active transport, response to TSH, and thyroglobulin synthesis and secretion. The FRTL-5 cells demonstrate high rates of iodide transport, enhanced TSH sensitivity, particularly after TSH starvation, and an ability to synthesize, secrete and iodinate thyroglobulin. These cells can lose their diploid characteristics while retaining functional characteristics, as described above, for a period of at least 1 year. However, after variable time periods, these non-diploid cells often lose responsiveness to autoantibody stimulators. Therefore, the uniformity of the FRTL-5 cells has been confirmed by periodic monitoring of the markers of normality, particularly chromosome number, and of differentiation.

A particular feature of the FRTL-5 cell strain, and one which both distinguishes it from its parent cell line and makes it invaluable in immunoassays, is its unique doubling time of 24–48 hours.

The FRTL-5 cells are grown in a medium supplemented with TSH, calf serum and, preferably, a mixture of other hormones, which hormone mixture preferably comprises insulin, hydrocortisone, transferrin, somatostatin and glycyl-L-histidyl-L-lysine acetate. These FRTL-5 rat thyroid cells, which are exquisitely sensitive to TSH-induced increases in cAMP levels, are derived from a parental FRTL cell line known to have an absolute dependency on the presence of TSH for cell growth. As a continuous culture strain, the FRTL-5 cells afford a means of defining their past history more clearly than primary cultures; as a strain derived from normal thyroids and devoid of malignant in vitro characteristics, they avoid issues raised in cultures in adenoma cells where growth is likely to be abnormally regulated by intrinsically altered properties of the cell. Although similar to the FRTL line as to normality and differentiation parameters, and somewhat similar in morphology, the FRTL-5 cells exhibit a much more rapid growth rate and a much higher cell density at or close to confluency.

The FRTL-5 thyroid cell culture system offers a readily available assay system to categorize Graves' IgG effector patterns by determining the separate stimulatory or inhibitory effects of an individual IgG on measurement of intracellular cAMP production, iodide uptake and labeled thymidine incorporation. The system can be utilized by any laboratory with tissue culture capability and affords the advantages of a stable cell type common to all laboratories, reproducibility of results and versatilty of assay design. The FRTL-5 thyroid cell culture system has also been shown to provide sensitivity equal to or greater than human slice and cell systems in detecting cAMP stimulatory antibodies. The system of the present invention also provides a major advantage over human cell systems in that it is additionally able to measure growth stimulating factors including autoantibodies.

Each of the three assays described herein provides information regarding the specific source or cause of a particular Graves' disease affliction. When employed in combination, two, and preferably three, of the assays permit a prognostic evaluation which permits more informed judgement as to the success of treatment involving drug therapy, surgery or radio-therapy. That is, the assays of the present invention permit detection of excess TSH growth-promoting antibodies as well as autoantibodies which stimulate or inhibit cyclic AMP production. The experiments of a number of workers in the field have suggested that immunoglobulins in the sera of patients with Graves' disease serve as the effector of thyroid overactivity.

The first of the three assays described herein using the differentiated FRTL-5 cells permits the detection of small amounts of thyroid stimulating autoantibodies and immunoglobulin Gs present in the sera of patients with Graves disease by measuring the elevation of cAMP levels. The cAMP assay is capable of measuring a stimulatory activity in LATS negative patients, that is, those patients which do not appear to exhibit the "species specificity" problems ascribed to that in vivo assay. In addition, this assay can measure autoimmune stimulating IgGs more readily than adenylate cyclase assays using human membrane preparations and does not appear to be significantly affected by the simultaneous presence of a TSH binding inhibitory activity in these IgGs. Thus, it appears that the "stimulating assay" employing FRTL-5 rat thyroid cells may become an effective tool for many laboratories interested in measuring thyroid stimulating autoimmune IgGs but limited in their ability to obtain human cell or slice material.

The second of the assays employing FRTL-5 cells described herein measures the uptake of iodide, a TSH stimulated and cAMP mediated transport phenomenon. From a clinical perspective, the iodide uptake assay may be simpler since it eliminates a time consuming and expensive radioimmunoassay required in the cAMP assay. It also appears to be slightly more sensitive than the cAMP assay and has the virtue of measuring a true thyroidal functional response. There is the possibility that, rather than a simple sensitivity question, IgGs which increase iodide uptake but not cAMP are a unique class of thyroid stimulating antibodies (TSAbs). Accordingly, it appears that both the cAMP assay and the iodide uptake assay complement, rather than substitute for, one another. Evidence also suggests that the iodide uptake assay may be used to detect TSAbs in thyroid diseases other than Graves' disease and possibly thyroid inhibitory factors as well.

The third assay of the present invention employs the continuous clonal strain of functioning rat thyroid cells, FRTL-5, to measure the growth stimulatory or inhibitory activity of IgG preparations from patients with autoimmune thyroid disease by determining labeled thymidine uptake. This assay system, like the cAMP and iodide uptake assays, may be utilized by any laboratory with tissue culture capability. When the thymidine uptake assay is used in conjunction with at least one of the cAMP assay or iodide uptake assay, analysis of patient sera permits three subclasses of patients afflicted with Graves' disease to be discerned: patients having sera containing IgG (a) with coexistent potent cAMP and growth activity; (b) with potent growth activity but low or nonexistent levels of cAMP stimulatory action; and (c) with potent cAMP enhancing action but low growth activity. It appears that not all of the autoimmune antibodies associated with Graves' disease respond in the same manner in the three assays, that is, each provides 80 to 90 percent positive responses, values comparable to most human thyroid cell and slice systems. Since, however, each of the assays may detect different antibodies, the composite effect of the IgG in the thymidine uptake assay and at least one of the cAMP or iodide uptake assays has better clinical predictive value than the activity in either assay alone, thus providing the capability of 100 percent positive tests. It provides, for the first time, a convenient means of evaluating the long term efficacy of drug therapy, such as thionamide therapy and/or the need for a surgical or radioiodine therapy.

The above background centers on the presence in Graves' autoimmune thyroid disease of antibodies which stimulate thyroid function and growth and are readily measured by the FRTL-5 assay system of the present invention. Other autoimmune thyroid diseases exist wherein inhibitors of thyroid function and growth are postulated to exist. The FRTL-5 system has been shown to be equally capable of measuring such inhibitors. In these cases the inhibitory activity is measured by including the suspected inhibitor with a known stimulator, for example, TSH or an autoimmune antibody stimulator.

BEST MODES FOR CARRYING OUT THE INVENTION

FRTL-5 Cell Strain

Figure 1:
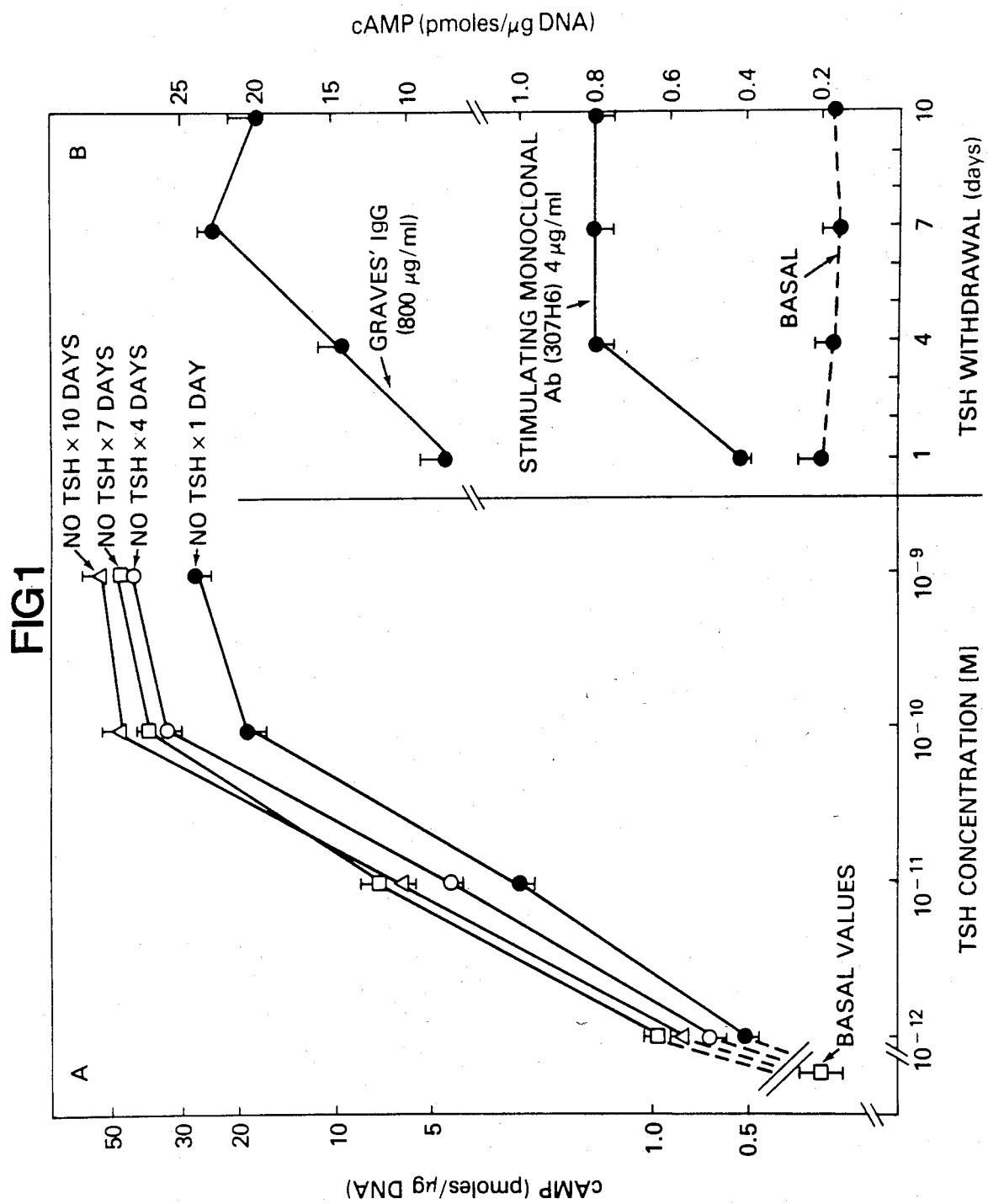
FIG. 1A graphically illustrates the ability of different concentrations of TSH to increase cyclic AMP levels in FRTL-5 cells whose growth medium has been depleted of TSH for increasing periods of time.
FIG. 1B graphically illustrates the ability of a Graves' serum IgG (top) or a Graves' monoclonal IgG (bottom) to increase cAMP levels in FRTL-5 cells whose growth medium has been depleted of TSH for increasing periods of time.

The FRTL-5 cell strain of the present invention is a cloned normal Fischer rat thyroid cell, deposited in the American Type-Culture Collection, Rockville, Md. and having the accession number ATCC CRL 8305. It is derived from FRTL cells, previously shown (Ambesi-Impiombato et al, "Culture Of Hormone-Dependent Functional Epithelial Cells From Rat Thyroids", *Proceedings of the National Academy of Science, USA*, 77, 6, pages 3455–3459, (1980)) to maintain the functional characteristics of iodide uptake, thyroglobulin synthesis and cyclic nucleotide metabolism over prolonged periods (two years) of culture. These cells have a TSH-responsive adenylate cyclase system and a TSH-stimulatable ADP ribosylation system.

The FRTL-5 cells are grown by placing FRTL-5 cells in Coon's modified Ham's F-12 medium supplemented with 2.5 to 15 percent by volume, preferably 5 percent by volume, calf serum and, preferably, a six hormone mixture comprising of 0 to 20 $\mu$g/ml, preferably 10 $\mu$g/ml, of insulin; 0 to $2\times10^{-8}$ M, preferably $10^{-8}$ M, of hydrocortisone; 0 to 10 $\mu$g/ml, preferably 5 $\mu$g/ml, of transferrin; 0 to 20 ng/ml, preferably 10 ng/ml, of glycyl-L-histidyl-L-lysine acetate; 0 to 20 $\mu$g/ml, preferably 10 $\mu$g/ml, of somatostatin; and 0.1 to 100 mU/ml, preferably 10 mU/ml, of TSH. Thus, the one hormone absolutely required for growing the FRTL-5 strain is thyrotropin. The cells are grown in air enriched with up to 7 percent but no less than 2 percent, preferably 5 percent by volume, of $CO_2$ at a temperature of 25 to 41 degrees C., preferably 37 degrees C.

The culture medium used is Coon's modification of Ham's F-12 supplemented with calf serum, fetal calf serum being found unsuitable for these cells. The culture medium and serum supplement are terminally sterilized by filtration through 0.22 μm Millipore filters. Prior to use, this medium is supplemented with a 60- to 100-fold concentrate of the sterile six hormone mixture. The complete supplemented medium has been designated mF12+6H to indicate that it is a 25 modified F-12 M formulation (Table I) supplemented with the mixture of six hormones.

TABLE I

| Composition of the Modified F-12 Medium (mF12) | | |
|---|---|---|
| | Concentration | |
| Component | mg/liter | mM |
| L-Arginine.HCl | 422.0 | 2.0 |
| L-Histidine.HCl | 42.0 | 0.2 |
| L-Isoleucine | 7.8 | 0.06 |
| L-Leucine | 26.2 | 0.2 |
| L-Lysine.HCl | 73.0 | 0.4 |
| Glycine | 16.0 | 0.2 |
| L-Methionine | 9.0 | 0.06 |
| L-Phenylalanine | 10.0 | 0.06 |
| L-Serine | 21.0 | 0.2 |
| L-Threonine | 23.8 | 0.2 |
| L-Tryptophan | 4.0 | 0.02 |
| L-Tyrosine | 11.0 | 0.06 |
| L-Valine | 23.4 | 0.2 |
| L-Cystine | 48.0 | 0.2 |
| L-Asparagine.HCl | 30.0 | 0.2 |
| L-Proline | 70.0 | 0.6 |
| L-Alanine | 18.0 | 0.2 |
| L-Aspartic Acid | 26.0 | 0.2 |
| L-Glutamic Acid | 30.0 | 0.2 |
| Sodium Pyruvate | 220.0 | 2.0 |
| Putrescine.2HCl | 0.3 | 0.001 |
| Biotin | 0.07 | 0.003 |
| Calcium Panthothenate | 0.5 | 0.001 |
| Niacinamide | 0.04 | 0.0003 |
| Linoleic Acid | 0.09 | 0.0003 |
| Pyridoxine.HCl | 0.06 | 0.0003 |
| Thiamine.HCl | 0.285 | 0.0008 |
| Riboflavin | 0.04 | 0.0003 |
| Folic Acid | 1.0 | 0.002 |
| Vitamin B-12 | 1.0 | 0.0007 |
| Thioctic Acid | 0.2 | 0.0009 |
| myo-Ionositol | 36.0 | 0.2 |
| Ascorbic Acid | 45.0 | 0.250 |
| Choline.HCl | 13.8 | 0.1 |
| Thymidine | 0.7 | 0.003 |
| Hypoxanthine | 4.0 | 0.030 |
| NaCl | 7530.0 | 130.0 |
| KCl | 305.0 | 4.0 |
| $Na_2HPO_4.7H_2O$ | 250.0 | 0.9 |
| $KH_2PO_4$ | 68.0 | 0.5 |
| $MgSO_4.7H_2O$ | 104.0 | 0.4 |
| $MgCl_2.6H_2O$ | 106.0 | 0.4 |
| $CaCl_2.2H_2O$ | 165.0 | 1.1 |
| $CuSO_4.5H_2O$ | 0.002 | 0.000008 |
| $ZnSO_4.7H_2O$ | 0.144 | 0.0005 |
| $FeSO_4.7H_2O$ | 0.8 | 0.0028 |
| Glucose | 2000.0 | 11.0 |
| $NaHCO_3$ | 2500.0 | 29.7 |
| Phenol Red | 1.25 | 0.0035 |
| Glutamine | 292.0 | 2.0 |

After the cells are grown to confluency, they are passaged bi-weekly. The passaging is done with a split ratio of between ⅛ to 1/15, preferably 1/10, using either trypsin alone or a 2 milliliter mixture of collagenase, 20 units per milliliter; trypsin (1:300), 0.75 mg/ml; heat-inactiviated dialyzed chicken serum, 2 percent in $Ca^{2-}$+and $Mg^{2+}$-free Hanks' Balanced Salt Solution (CTC solution). When uniform-cell suspensions are desired, this solution is made 2 mM in ethylene glycol bis (beta-aminoethyl ether)-N, N, N', N'-tetraacetic acid, which is added as a 0.2 M solution in 1 M NaOH/$Ca^{2+}$-and $Mg^{2+}$-free Hanks' Balanced Salt Solution, 1:1.

The strain of differentiated FRTL-5 cells of the present invention is derived from a parent FRTL cell line which also maintains the functional characteristics of iodide uptake and thyroglobulin synthesis over prolonged periods of culture, also has a TSH-responsive adenylate cyclase and ADP ribosylation system, and also has an absolute growth requirement for TSH. Unlike the FRTL-5 cells, however, the FRTL cell line is slow growing, having a doubling time of 5-7 days. The FRTL-5 strain may also be distinguished from the FRTL line by the latter's limited ability to survive TSH withdrawal for more than 24 to 48 hours and its morphologic inability to achieve confluency, but rather exists only as isolated sparse colonies. It may be further noted that FRTL cells, when comparably seeded and grown in a 100 mm Petri dish for a period of 1 to 2 months, achieved its maximum growth of less than $5 \times 10^6$ cells, whereas FRTL-5 cells grown to confluency under identical conditions, except for serum concentration, attained a cell number of approximately $5 \times 10^7$ cells in a 100 mm Petri dish in a period of less than 1 month.

The FRTL cells themselves may be obtained as described in F. S. Ambesi-Impiombato et al, "Culture Of Hormone-Dependent Functional Epithelial Cells From Rat Thyroids", *Proceedings of the National Academy of Science, USA*, 77, 6, pages 3455-3459. Specifically, cell dissociation procedures are used which are similar to those now in standard use for the isolation of primary cell lines. Thus, thyroid glands are excised from 5- to 6-week-old normal Fischer rats that are killed by $CO_2$ asphixiation. Normally, the glands from 3 to 6 rats are pooled and used for primary cultures. All the procedures are performed under sterile conditions. The glands are freed from adherent connective tissue, cut into small pieces, and washed in $Ca^{2+}$- and $Mg^{2+}$-free Hanks' Balanced Salt Solution by centrifugation at approximately 500 ×g. Enzymatic digestion is carried out by adding to the washed pellet, 2 ml of a mixture of collagenase, 20 units per ml; trypsin (1:300), 0.75 mg/ml; heat-inactivated, dialyzed chicken serum, 2 percent in $Ca^{2+}$- and $Mg^{2+}$-free Hanks' Balanced Salt Solution (CTC solution). The tissue is thereafter incubated for approximately 20 minutes at 37 degrees C. in a vigorously shaking water bath. Usually, two 20 minute incubations and some vigorous pipetting are sufficient to reduce the whole tissue mass to a cell suspension. After a 2 minute settling period, which allows fragments to settle, the supernatants are collected, combined, washed in complete medium and distributed into 10-cm Falcon plastic tissue culture dishes at $10^4$ to $10^5$ cells per dish. Secondary cultures are made by transferring individual epithelial colonies with cloning cylinders. The culture medium used is essentially the same as that described above for culturing FRTL-5 cells, that is, Coon's modified Ham's F-12 supplemented with the mixture of six hormone and calf serum, except that the calf serum is present in an amount of 0.1 to 0.5 percent rather than 5 percent.

The related strain of Fischer rat cells, FRT, may be isolated from primary cultures of Fischer rat thyroid glands of 6-week-old litter mates of NIH Fischer 344 inbred strain of rats, that is, the same strain of rats from which the FRTL cell line is isolated by isolation in medium supplemented with 5 percent serum and dibutyryl cyclic AMP and thereafter "conditioning" by a culture on thyroid fibroblasts for 24 hours. These cells are able to produce thyroglobulin in primary cultures but after adaptation to growth in unconditioned medium they lose the ability to concentrate iodide or to produce thyroglobulin.

Cyclic AMP Assay

FRTL-5 cells may be used to assay thyrotropin and GD IgG preparations obtained from patients sera by measuring the increase in cAMP content and will demonstrate positive responses even in situations in which in vivo mouse assays and human membrane assays are negative.

In conducting the cAMP assays, the following procedure is generally used. FRTL-5 rat thyroid cells grown and prepared as described above are plated in a medium which includes calf serum and TSH. Preferably, the plating medium also includes a mixture of five hormones (5H) which includes insulin, hydrocortisone, transferrin, glycyl-L-histidyl-L-lycine acetate, and somatostatin. The calf serum in which the cells are plated is present in an amount of about 2.5 to about 15 percent, by volume, preferably 5 percent by volume.

Although thyrotropin may be removed from the plating medium without any intermediary steps, it is preferred that the FRTL-5 cells undergo a growth period after plating of between 1 to 10 days. During the growth period, the five hormone mixture described above is preferably added. The TSH is most effectively removed by washing the cells with an isotonic buffer or a nutrient medium or either one of the foregoing with calf serum.

Although at least one thyroid stimulatory, inhibitory or combination of factors (which factors may be obtained from patient IgG) may be added directly to the FRTL-5 cells shortly after removal of TSH, the cells are preferably maintained in a thyrotropin-free medium for a period of about 1 to about 10 days, preferably 7 to 10 days, before introducing the thyroid factors. During this period, the cells are preferably maintained in the five hormone mixture described above. The thyrotropin-free medium preferably includes Coon's modified F-12 medium and about 2.5 to about 15 percent, preferably 5 percent, by volume, of calf serum.

After thyrotropin-free medium is removed, a buffered medium and at least one thyroid stimulatory factor, inhibitory factor or a combination of the foregoing factors is added to the FRTL-5 thyroid cells. After introducing the thyroid factors to the cells, an inhibitor of cAMP phosphodiesterase activity is added. The inhibitor is preferably 3-isobutyl-1-methylxanthine (IMX). At or shortly after the thyroid factors are introduced to the cells, a proteinaceous substance which prevents non-specific adsorption of the thyroid factors to the assay vessel is added. Preferred non-specific adsorption preventing materials include bovine serum albumin, egg albumin and gelatin.

After introduction of the thyroid factors, the cells are incubated in the buffered medium with the thyroid factors for a period preferably of 3 hours. The buffered medium employed in the incubation step is preferably a phosphate buffered saline solution or Hanks' Balanced Salt Solution (HBSS). Most preferably, this buffered medium is reduced in salt content or substantially free of sodium chloride.

The reactions occurring during incubation are terminated by aspiration of the buffered medium containing the thyroid factors. cAMP is detected, preferably by a radioimmunoassay in either the aspirated medium (extracellular cAMP) or in the cells remaining in the incubation vessel (intracellular cAMP). Recovery of intracellular cAMP may be accomplished most effectively by adding an agent to the cells remaining in the incubation vessel which precipitates protein-containing material, by separating the precipitated protein-containing material from the supernatant liquid and by analyzing the supernatant liquid for cAMP. Ethanol is the preferred agent to employ in precipitating the protein and dissolving cAMP. Ethanol at below 0 degrees C. may be added to the incubation containing buffered medium and thyroid factors without prior aspiration; in this case the cAMP radioimmunoassay of supernatant liquid will measure the sum of intracellular and extracellular cAMP. In order to compensate for differences in the number of cells originally plated in each assay well, the separated protein-containing material may be analyzed for protein per se or for DNA.

The optimum conditions for performing the cyclic AMP assay are as follows: The FRTL-5 cells are grown in 24-well Costar plates for 2 to 7 days before switching to the five hormone medium. The FRTL-5 cells are prepared for assays measuring TSH or autoimmune IgG stimulatory activity by removing the six hormone media in which they are grown by suction and cells are thereafter washed twice with the above-described five hormone mixture, i.e., media without TSH, or, alternatively, Coon's modified F-12 medium with 5 percent calf serum and are then maintained in this same media. After a period of 7 to 10 days of maintenance in the five hormone medium, cells are washed twice with Hanks' Balanced Salt Solution (HBSS) and GD IgG preparations isolated from patient sera (discussed below) are added and diluted in HBSS containing 0.4 percent bovine serum albumin (BSA). Alternatively, improved results may be obtained employing a hypotonic medium with approximately 1/10 the HBSS concentration or using an isotonic medium where 0.2 M sucrose replaces all but 1/10 of the HBSS. Incubations are initiated and continued for a period of 30 minutes to 3 hours at a temperature of 37 degrees C. in the presence of 0.5 mM 3-isobutyl-1-methyl-xanthine (IMX). The reaction is terminated by aspiration of the incubation medium, which is saved, addition to the cells of between 250 to 600 microliters of cold absolute ethanol, and storage of the cells overnight at a temperature of between about $-15$ to $-30$ degrees C., preferably -20 degrees C. Aliquots of the aspirated incubation medium are immediately analyzed for cAMP by their direct inclusion in the cAMP assay or, alternatively, are dried overnight at room temperature, reconstituted with an assay buffer of approximately 0.05 M sodium acetate, pH 6.2, and then included in the cAMP assay. The cAMP is measured using a radioimmunoassay (RIA, such as Becton Dickinson radioimmunoassay). The ethanolic supernatant may be aspirated from the cells by suitable means. Alternatively, the cells are scraped, the mixture transferred to microfuge tubes with a single cold absolute ethanol wash, and the cell debris removed by centrifugation. If intracellular cAMP is to be measured by radioimmunoassay, aliquots of the ethanolic supernatant are dried and reconstituted with an assay buffer of approximately 0.05 M sodium acetate, pH 6.2. DNA content is measured in the cell debris remaining in the incubation vessel or in the pellet by the diphenylamine method as described by Kissane et al, "The Fluorometric Measurement Of Deoxyribonucleic Acid In Animal Tissue With Special Reference To The Central Nervous System", *Journal Of Biological Chemistry*, 233, page 184 (1958). Results are reported as picomoles, cyclic AMP/microgram DNA. All assays are normally run with a positive TSH control, a "no addition" control, i.e., buffer alone, and a control using normal IgG prepared from a pool of 10 to 20 normal individuals.

Rather than DNA, protein may be measured using a colorimetric method as described by Lowry et al, "Protein Measurement With the Folin-Phenol Reagent", *Journal Of Biological Chemistry*, 193, page 265 (1951).

Purified GD IgG is prepared from patient sera by double chromatography on DEAE-Sephadex using the Baumstark technique (Baumstark et al, "A Preparative Method For The Separation Of 7S Gamma Globulin From Human Serum", *Archives Of Biochemistry And Biophysics* 1964, 108, pages 514–520). IgG is concentrated by ammonium sulfate concentration and extensively dialyzed against a suitable buffer, such as 20 mM phosphate buffer, pH 7.2, phosphate buffered saline having a pH of 7 to 7.4, or Hanks' Balanced Salt Solution. Each GD IgG is terminally sterilized by passage through a Millipore 0.2 micron filter.

Alternatively, crude GD IgG preparations may be prepared using a polyethylene glycol precipitation procedure. To 1 ml serum is added 473 microliters of 50 percent polyethylene glycol. After a 30 minute incubation, tubes are centrifuged at $3,000 \times g$ for 10 minutes. The precipitate is washed with 1 ml of 15 percent polyethylene glycol and resuspended in 2 ml of Hanks' Balanced Salt Solution, all procedures being performed at 4 degrees C.

The time of TSH withdrawal from FRTL-5 cells growing in continuous culture immediately prior to performing a cAMP assay determines in part the sensitivity of response to acute TSH or GD IgG challenge. Basal cAMP levels decline and acutely stimulated cAMP production increases as TSH starvation is prolonged. This conclusion is supported by the results summarized and depicted in FIG. 1A. As TSH deprivation is extended from 1 to 10 days, the cAMP response to acute TSH challenge increases approximately 2-fold. The response sensitivity, that is, the detection limit, increases 5- to 10-fold between day 1 and day 10 from approximately $0.5 \times 10^{-12}$ M to $0.5 \times 10^{-13}$ M TSH. Basal cAMP levels (approximately $0.18 \pm 0.05$ picomoles/micrograms moles/micrograms DNA) change only slightly after the first 2 days of maintaining cells in the TSH deprived media, i.e., the five hormone media.

In a similar fashion, the data represented in FIG. 1B illustrates that a heterohybridoma Graves' monoclonal stimulating antibody, designated #307H6, or the heterogeneous GD IgG preparation derived from a patient's serum both induced a 2- to 5-fold greater rise in intracellular cAMP production with a maximal sensitivity between days 4 and 7 of TSH starvation, this being the minimum preferred duration of starvation. Substantially the same results have been obtained measuring extracellular cAMP production.

Figure 2:
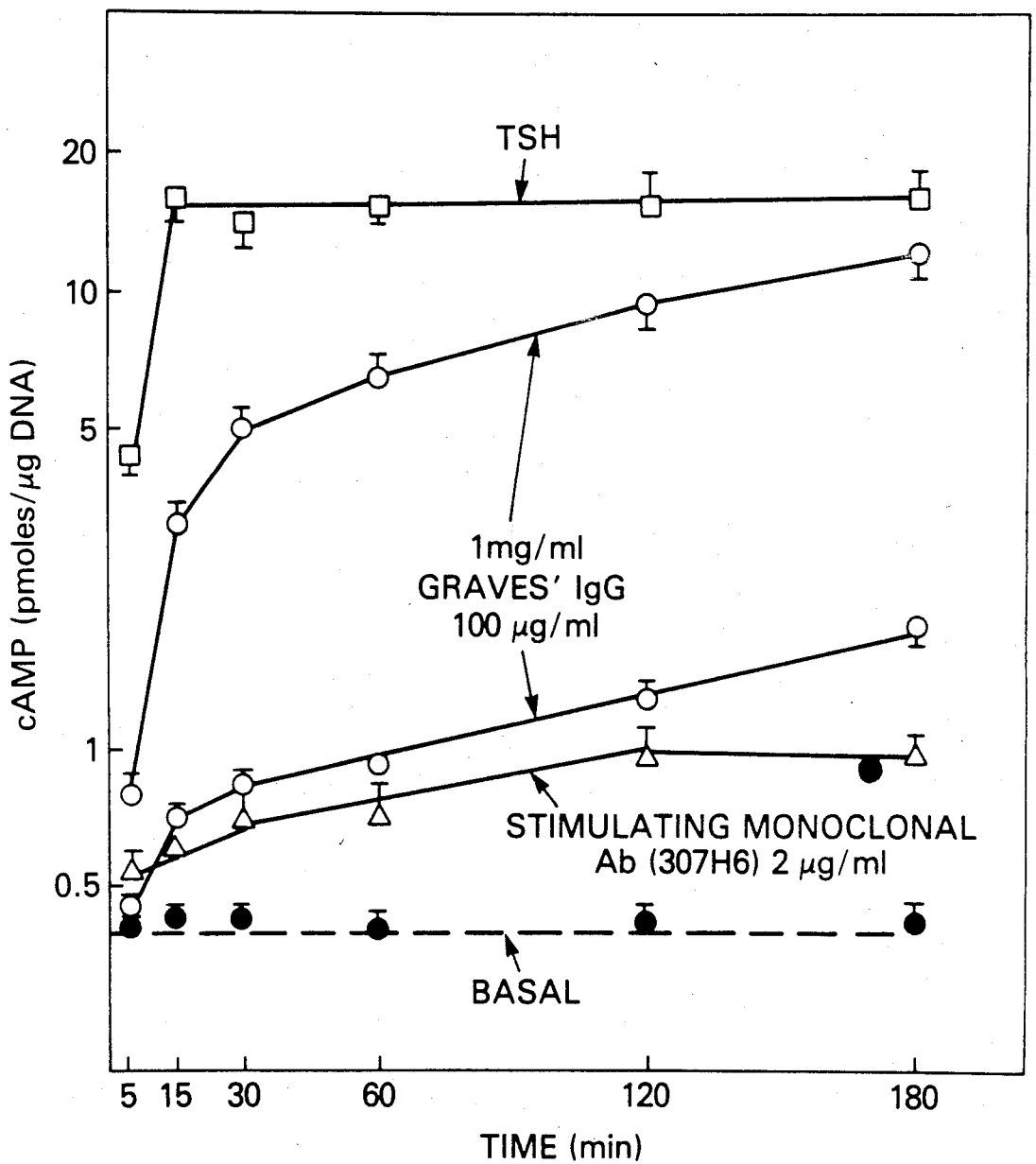
FIG. 2 graphically illustrates the increase in cAMP levels at different times after FRTL-5 cells are incubated with TSH, a Graves' serum IgG at two different concentrations, and a Graves' monoclonal stimulatory antibody, the FRTL-5 cells having been maintained in TSH-free medium for 7 days.

The time course, or response time, for the Graves' heterohybridoma stimulating monoclonal IgG, GD IgG preparation isolated from patient serum, and for TSH stimulated cAMP production is shown in FIG. 2. TSH induces a rapid rise with a plateau effect noted by about 15 minutes after incubation. By comparison, the GD IgG demonstrates a delayed effect with maximal response between 2 and 3 hours. No further increase in cAMP production is generally observed after 3 hours. It should be noted that the value of 2 micrograms/ml for the monoclonal antibody 307H6 represents the true concentration of specific human stimulatory IgG, whereas the 100 micrograms/ml for the GD IgG derived from patient serum represents total IgG protein.

Figure 3:
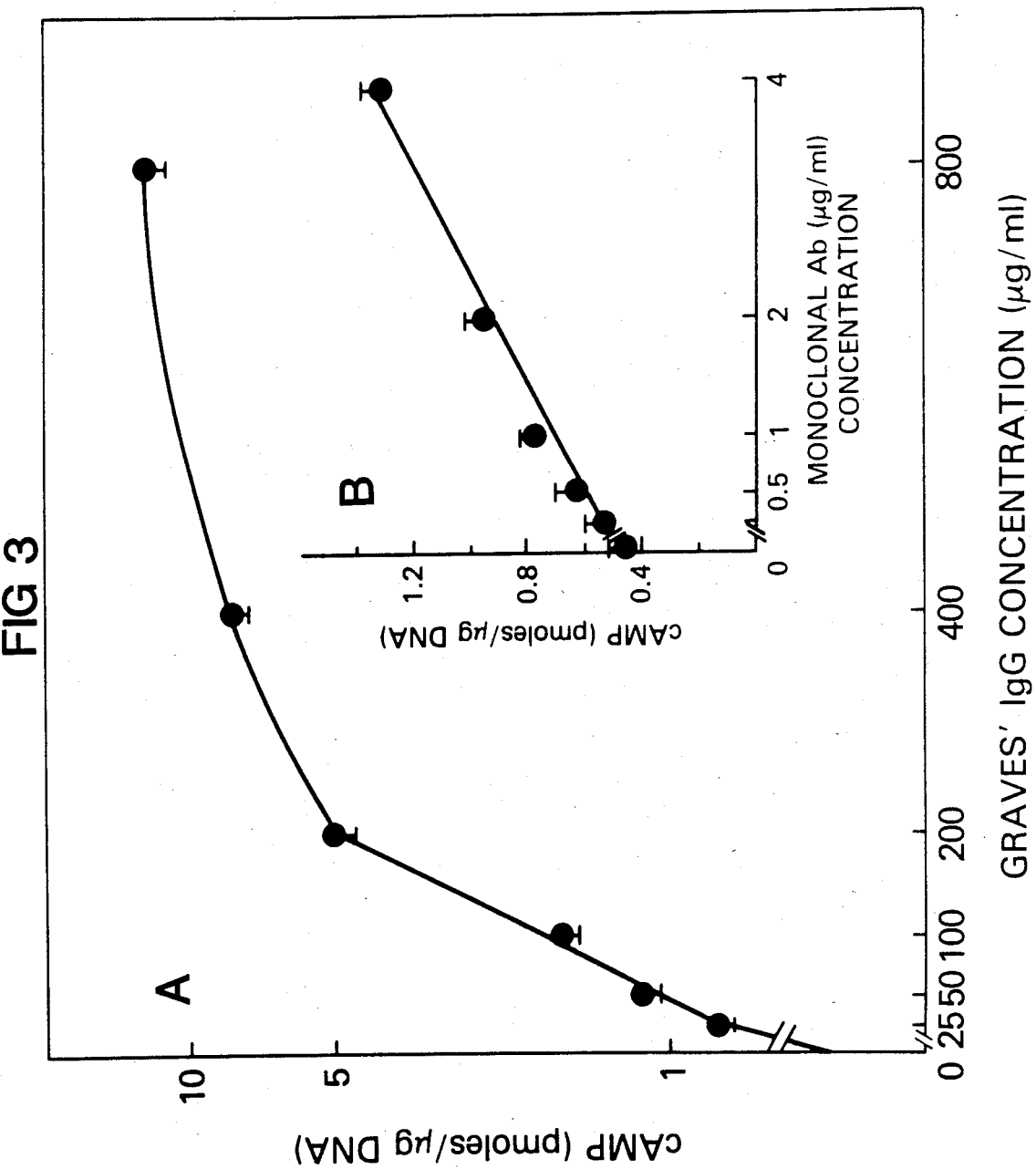
FIG. 3 graphically illustrates the increase in cAMP levels induced in FRTL-5 cells after 2 hours of incubation with different concentrations of (a) Graves' serum IgG or (b) a Graves' monoclonal stimulatory IgG, the FRTL-5 cells having been maintained in TSH-free medium for 7 days.

Dose response curves for both the Graves' heterohybridoma stimulating monoclonal antibody 307H6 and GD IgG obtained from patient serum are presented in FIG. 3. Significant stimulation by Graves' monoclonal antibody 307H6 is evident at concentrations as low as 0.5 micrograms/ml and increases in a linear fashion through the maximum concentration tested, 4 micrograms/ml. Other monoclonal stimulators also demonstrate linearity at concentrations as high as 20 micrograms/ml. As may be noted from FIG. 3, the GD IgG preparation obtained from patient serum exhibits linearity at up to 200 micrograms/ml total protein concentration and is maximal at 800 micrograms/ml total protein concentration. Comparable concentrations of normal bovine, mouse and human IgG preparations had no affect on the basal cAMP level in FRTL-5 cells.

The procedure used for seeding cells prior to performing assays is somewhat important to maximize the sensitivity of the response. Thus, if cells are trypsinized and seeded directly in the five hormone medium, they attach well but do not grow well. The response to acute challenge with TSH is significantly lower and is not increased with prolonged maintenance in the five hormone medium. By day 10, cell response is less than half of that at days 1 and 4. The optimal TSH stimulation of FRTL-5 cell cAMP levels is also dependent on the number of cells per well. The optimal cell number for standard experiments is generally in the range of between about $5 \times 10^4$ and $5 \times 10^5$ cells/well.

The most important factors in optimizing conditions for the cAMP assay thus include:

(1) prolonged exposure (7 to 10 days) of the FRTL-5 cells to a non-growth medium, i.e., one without TSH after initial trypsinization and seeding (2 to 4 days) in the usual six hormone medium;

(2) the time for detecting stimulation (2 to 3 hours);

(3) the number of cells per well ($5 \times 10^4$ to $5 \times 10^5$);

(4) the IgG concentration (250 to 500 micrograms/ml is preferred with 10-fold higher and lower concentrations likely to provide a reasonable concentration range to exhibit dose dependent effects); and (5) use of media reduced in salt concentration or substantially free of sodium chloride and containing 0.5 mM IMX.

Using these optimum conditions, the detection of stimulatory activity in GD IgG preparations from sera indicates positive results in approximately 90 percent of sera tested.

Iodide Uptake Assay

The uptake of iodide by FRTL-5 thyroid cells is TSH stimulated and cAMP mediated. From a clinical point of view, the iodide uptake assay may be simpler than the cAMP assay since it eliminates a time consuming and expensive radioimmunoassay. The iodide uptake assay also appears to be slightly more sensitive and has the virtue of measuring a true thyroidal functional response. Since it has not yet been unequivocally established that the GD IgGs which increase iodide uptake do so solely as a result of their ability to stimulate production of cAMP, both assays may be complementary rather than a substitute of one for the other.

The procedure for performing the iodide uptake assay is generally the same as the cAMP assay in all respects with the following exceptions noted. A nutrient medium, rather than a buffered medium, is used in the step in which the thyroid stimulatory or inhibitory factors are introduced and in the incubation step which follows immediately thereafter and is carried on for a period of 36 to 48 hours. After the incubation step and prior to termination of the biochemical reactions, a source of radioactive iodide is added to the incubated mixture and a second incubation is performed in a buffered medium. Thereafter, the second incubation is terminated, the radioactive iodide, which is a soluble radioiodide salt, preferably $Na^{125}I$ or $Na^{131}I$, is recovered and detection of radioactive iodide is performed by a suitable detection means. The medium employed in the first incubation is removed by washing, preferably with a sodium ion-containing isotonic buffered medium, which buffered medium contains a modified Hanks' Balanced Salt Solution. The second incubation, in which radioactive iodide is present, is performed for a period of 20 to 60 minutes, preferably in a sodium and potassium ion-containing buffered medium. This sodium and potassium ion-containing buffered medium is also, preferably, a modified Hanks' Balanced Salt Solution.

The optimized procedure for performing the iodide uptake assay for detecting thyroid stimulatory or inhibitory factors is as follows: FRTL-5 thyroid cells are seeded and thereafter grown in the absence of TSH for 10 days, as described above. Fresh media is added to the cells containing 0.005mM 3-isobutyl-1-methyl xanthine (IMX) and about 1 to 5 mg/ml of crude GD IgG (prepared by a polyethylene glycol precipitation procedure) or about 250 µg/ml to 5 mg/ml of purified GD IgG (obtained by double chromatography on DEAE-Sephadex) isolated from patient sera. After a period of approximately 30 to 60 hours, preferably 36 to 48 hours, culture medium is removed and cells are washed with approximately 1 ml of modified HBSS having a composition of 137 mM NaCl, 5.4 mM KCl, 1.3 mM $CaCl_2$, 0.4 mM $MgSO_4.7\ H_2O$, 0.5 mM $MgCl_2$, 0.4 mM $Na_2HPO_4.7\ H_2O$, 0.44 mM $KH_2PO_4$, 5.55 mM glucose, and 10 mM Hepes, pH 7.3. The assays are initiated by overlaying the cells with approximately 200 to 750 microliters, preferably 500 microliters, of the modified HBSS containing suffrcient carrier-free $Na^{125}I$ and 10 µM NaI to give a specific activity for $^{125}I$ of 20 mCi/mmol. The reactions are carried out at a temperature of 25 to 37 degrees C., preferably at 37 degrees C., in a humidified atmosphere and are terminated after 20 to 40 minutes, preferably 30 minutes, by aspirating the radioactive medium, washing with approximately 1 ml of ice-cold modified HBSS, treating the cells with approximately 1 ml of 95 percent ethanol for a period of approximately 10 to 30 minutes, preferably 20 minutes, counting the extracted material in a scintillation counter or a Beckmann 9000 gamma counter, and measuring the DNA content of the ethanol precipitated cell debris. Nonspecific uptake may be measured in duplicate assays incubated in the presence of IMX-media alone or containing normal human IgG at the same protein concentrations. Positive controls are assays which include TSH ($1\times10^{-11}$ to $1\times10^{-9}$ M).

Figure 4:
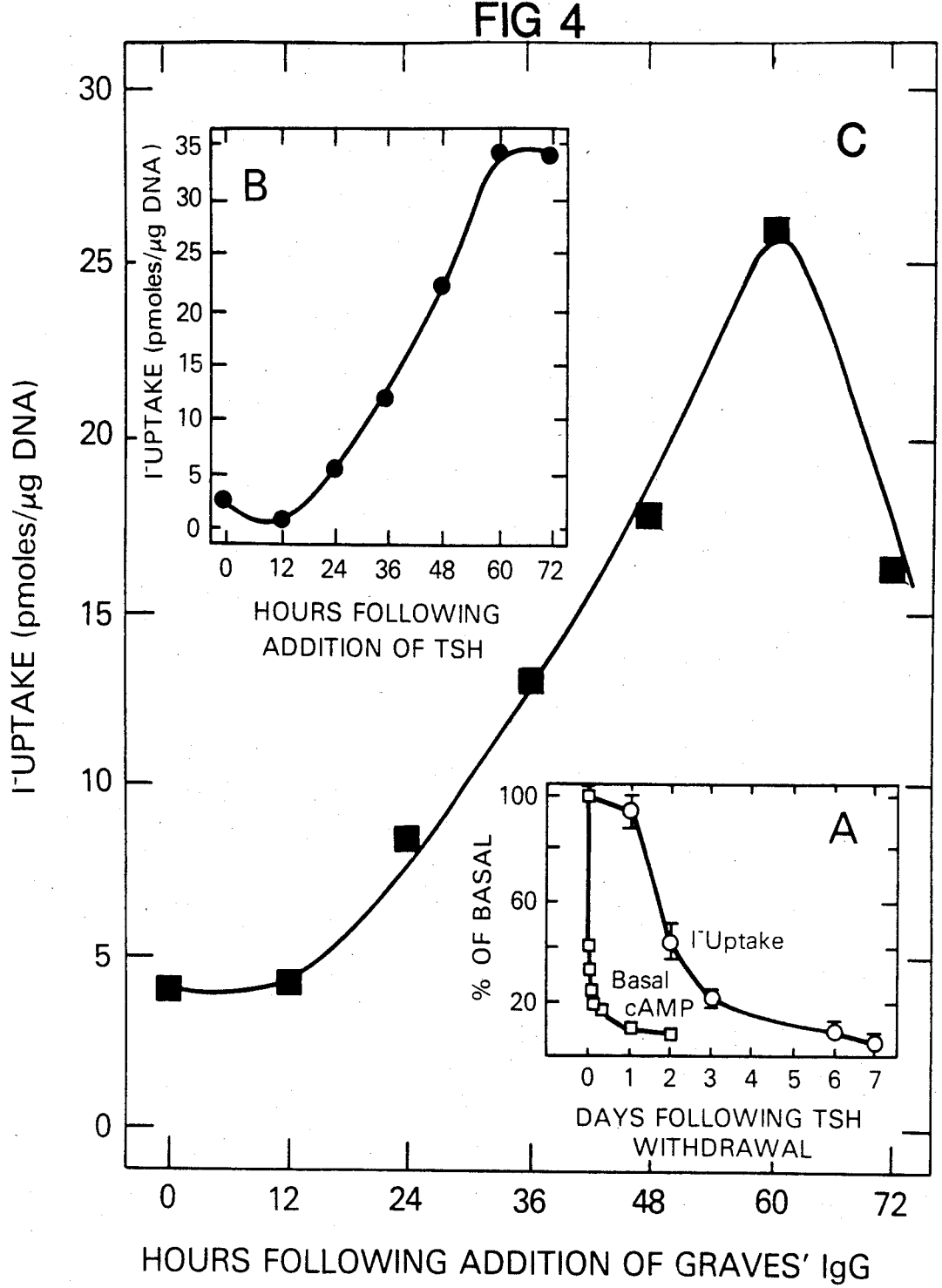
FIG. 4A graphically illustrates the decrease in cAMP levels and in iodide uptake in FRTL-5 cells at different days after TSH is withdrawn from the growth medium.
FIG. 4B graphically illustrates iodide uptake by FRTL-5 thyroid cells following the readdition of TSH to the incubation medium of cells, which medium was previously depleted of TSH for 7 days.
FIG. 4C graphically illustrates the iodide uptake by FRTL-5 thyroid cells following the addition of a Graves' serum IgG to the incubation medium of cells, which medium was previously depleted of TSH for 7 days.

Removal of TSH from the growth medium of FRTL-5 cells results in a rapid decline in cAMP levels but a more gradual loss in their ability to take up iodide, as is illustrated in FIG. 4A. Readdition of TSH-containing 6H medium (FIG. 4B) or GD IgG obtained from patient serum (TSAb) (FIG. 4C) results in a gradual return of iodide uptake toward control levels, i.e., toward the level prior to the depletion period. In both cases, a lag period of 12 hours is evident, maximal return of iodide uptake occurring by approximately 60 hours.

Several differences may be noted between TSH and GD IgGs with respect to iodide uptake by FRTL-5 cells. Unlike TSH, GD IgGs do not cause the initial decrease in iodide uptake between 0 and 12 hours observed here (FIG. 4C vs FIG. 4B). Further, GD IgG maximal uptake level is immediately followed by a downward trend in iodide uptake (FIG. 4C), whereas TSH results in a stable plateau level after 60 hours (FIG. 4B) which persists for days. The rate of iodide uptake is faster with GD IgG than with TSH. TSH need not be present more than 5 hours to stimulate full return of iodide uptake to control levels as compared to GD IgG which must be present over a much longer period to achieve its maximal effect. Like TSH, the ability of GD IgG to return iodide uptake toward control levels is dependent on the concentration of GD IgG added to the incubation period. Return of iodide uptake to half maximal values requires significantly less GD IgG in contrast to return of cAMP values toward maximum. Significant iodide uptake, i.e., uptake clearly above controls, is also evident at significantly lower concentrations than in assays measuring the ability of GD IgG to elevate cAMP levels. This "amplification" aspect is also evident using TSH under identical conditions, i.e., in the presence of 0.005 mM rather than 0.5 mM IMX concentrations as is usual in cAMP cell assays.

Thymidine Incorporation Assay

In addition to using the differentiated, functional line of rat thyroid cells in continuous culture, the FRTL-5 cell line, to measure cAMP stimulating autoimmune thyroid antibodies or GD IgGs, the same cells may also be used as a convenient measure of TSH stimulated growth activity by a determination of labeled thymidine uptake.

The thymidine incorporation of the cells is determined generally as follows: FRTL-5 cells are grown and prepared as described above. They are then plated in a medium which includes calf serum and TSH. This plating medium may also include a mixture of hormones comprising insulin, hydrocortisone, transferrin, glycyl-L-histidyl-L-lycine acetate, and somatostatin.

Although not mandatory, the FRTL-5 cells may be subjected to a growth period after plating, most suitably for a period of between about 1 to 10 days. During the growth period, the plating medium may be supplemented with a mixture of hormones which, preferably, includes insulin, hydrocortisone, transferrin, glycyl-L-histidyl-L-lycine acetate, and somatostatin.

Either after the plating step or, preferably, the growing period, TSH is removed from the plated cells. This may generally be done by washing the cells with an isotonic buffer or a nutrient medium, either one of the foregoing containing calf serum. After removal of thyrotropin from the plated cells, labeled thymidine, a nutrient medium and one or more thyroid stimulatory factors or inhibitory factors are added to the plated FRTL-5 cells. Although this step may be performed shortly after removal of TSH, it is preferred to maintain the cells in a thyrotropin-free medium after removal of thyrotropin and before addition of the labeled thymidine and thyroid factors. This thyrotropin-free maintenance period is preferably from about 1 to about 10 days and most preferably for about 5 days. Assay results are generally improved if the mixture of five hormones, described above, is added during this TSH-free maintenance period and the TSH-free medium is changed at least once during this period. The nutrient medium containing the thyroid cells, labeled thymidine, and thyroid stimulatory or inhibitory factors preferably includes Coon's modified F-12 medium described above. The nutrient medium also preferably includes about 2.5 to about 15 percent, by volume, of calf serum, preferably about 5 percent by volume. The thymidine is preferably labeled with $^3H$ or $^{14}C$.

The above-described mixture of FRTL-5 thyroid cells, labeled thymidine, nutrient medium and thyroid stimulatory or inhibitory factors is incubated in a medium which, preferably, includes the five hormone mixture described above for a period of preferably 72 hours.

After incubation, growth of the FRTL-5 cells is terminated with a suitable buffer solution, which buffer solution is, preferably, a phosphate buffered saline solution or Hanks' Balanced Salt Solution (HBSS). The growth terminating buffer solution is normally maintained at a temperature of about 1 to about 4 degrees C.

Incorporated labeled thymidine is recovered and detected by a suitable radioactive detection means. Recovery of labeled thymidine may be accomplished by adding an agent which precipitates protein-containing material. The supernatant liquid containing the labeled thymidine may then be removed by suitable means and analyzed. Preferred protein-precipitating agents include trichloroacetic acid and ethanol. To minimize erroneous results from variations in the number of cells from well to well, the protein-containing material is preferably determined either for protein per se or for DNA.

For optimization of the thymidine incorporation assay, the following procedure is generally followed: FRTL-5 cells grown for 2 to 7 days in Coon's modified Ham's F-12 medium containing 5 percent calf serum and the six hormone mixture, described above, are washed several times in 1 ml of HBSS before medium containing 5 percent calf serum and the five hormone mixture (TSH omitted) is added. The cells are maintained in the five hormone medium without TSH for a period of 1 to 10 days, preferably 5 days. The wells containing the cells are washed again with HBSS and thereafter are added about 250 to about 750 microliters, preferably 500 microliters, of fresh medium containing 5 percent calf serum and the five hormone mixture; approximately 100 to 500 microliters, preferably 200 microliters, of GD IgG preparation (approximately 2.5 mg); and 1 to about 10 microliters of [$^3H$]- or [$^{14}C$]-labeled thymidine (0.5 to about $2 \times 10^6$ cpm). The plates are incubated for a period of about 18 to about 96 hours, preferably 72 hours, at a temperature of about 25 to 37 degrees C., preferably 37 degrees C. in 5 percent $CO_2$/95 percent air, humidified atmosphere. Thymidine uptake is terminated by a double wash with cold phosphate buffered saline solution (PBS), pH 7.2 to 7.4, and thereafter approximately 1 ml of ice-cold 5 percent trichloroacetic acid is added. After approximately 10 minutes at 4 degrees C. the supernatant is aspirated and approximately 800 microliters of diphenylamine solution is added. This solution consists of approximately 5 grams diphenylamine in 450 ml glacial acetic acid plus 10 ml sulfuric acid which in toto is mixed 20:8 (volume/volume) with water and with 0.1 volume of 1 percent fresh acetaldehyde in water. After overnight development at room temperature, aliquots of each well are analyzed for DNA content by absorbence at 580 nm using spermine DNA standards and for labeled thymidine content. Since thymidine is radioactively labeled, its content may be determined by the radioactivity measured by means of liquid scintillation spectrometer. Preferred radioactive labels include tritium, labeled on methyl, or $^{14}C$.

As noted above, the thymidine uptake assay is a convenient measure of growth. Assays which measure cell number, total DNA, total protein, etcetera, may be used with the FRTL-5 cells for the same purpose. Although a less efficacious and more time consuming evaluation of thymidine incorporation than using labeled thymidine, an alternative procedure for such evaluation would include cell counting. The unique aspect of the FRTL-5 assay system is the TSH dependent growth exhibited by these cells which can be quantified and the fact that a population of TSAbs exists which stimulates growth of thyroid cells rather than cAMP metabolism.

The FRTL-5 thyroid cells exhibit an absolute TSH requirement for growth. Removal of TSH from the medium results in a static, non-growing culture which could regain its TSH growth response so long as cells are in a non-confluent state. Thus, whereas it is preferred to use cells grown to or near confluency for the cAMP and iodide uptake assays, the thymidine incorporation assay requires a non-confluent state. To avoid problems of confluency, cells used to measure thymidine incorporation are grown in 12-well plates, that is, plates with larger surface areas, rather than the 24-well plates employed in the cAMP and iodide uptake assays.

The evidence indicates that there is a growth correlation between IgG stimulated 72 hour thymidine uptake and cell growth, i.e., the magnitude of the individual IgG effects on 72 hour thymidine uptake parallels the individual effects on growth rate as measured by cell number. TSH stimulated growth and thymidine uptake has also been noted to exhibit a 48 hour time lag when studies are performed using cells whose growth medium has been TSH depleted for prolonged periods. On the other hand, withdrawal of TSH for at least 2 days is necessary to achieve a clearcut cessation of growth and 4 days to achieve low basal thymidine uptake values. Accordingly, a 5 day period of TSH withdrawal is preferred to initiate experiments and a 72 hour simultaneous exposure of cells to TSH or IgG is preferred as a convenient compromise for routine assays.

Figure 5:
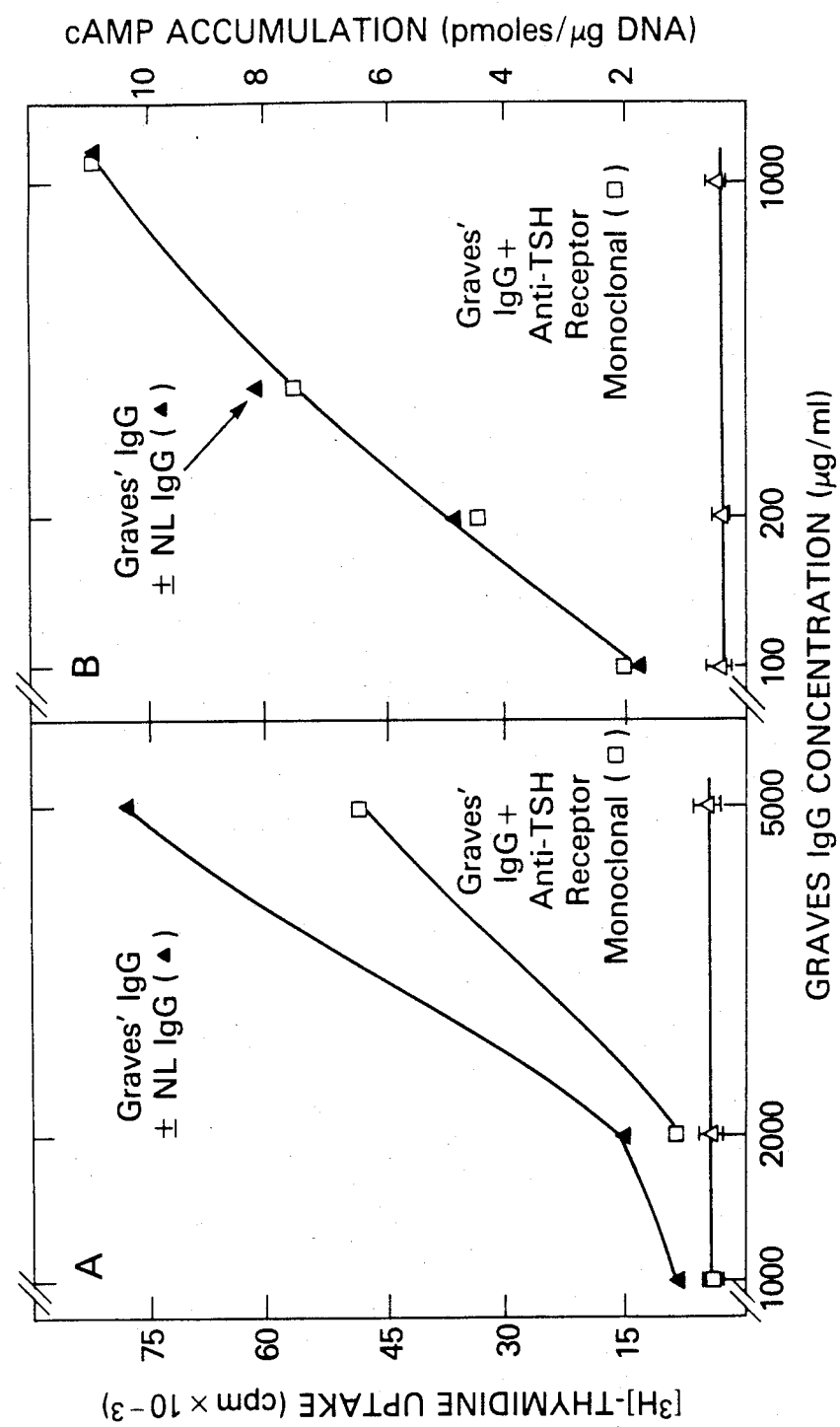
FIG. 5A graphically illustrates radioactive thymidine uptake by FRTL-5 cells caused by increasing concentrations of a Graves' serum IgG in the absence or presence of a normal (NL) IgG or of a monoclonal antibody to the TSH receptor, the FRTL-5 cells previously maintained in TSH-free medium for 5 days.
FIG. 5B graphically compares the ability of the Graves' serum IgG of FIG. 5A to increase cAMP levels in the absence or presence of a monoclonal antibody to the TSH receptor, the FRTL-5 cells being maintained for the same time period and under identical conditions in the TSH-free medium as in FIG. 5A.

As illustrated in FIG. 5, the effect of GD IgG preparation on thymidine uptake exhibits concentration dependence.

EXAMPLE 1

FRTL-5 Rat Thyroid Cells In Continuous Culture

The FRTL-5 cell line, a cloned line of normal rat thyroid cells derived from FRTL cells, was grown in Coon's modified Ham's F-12 medium supplemented with 5 percent calf serum and a six hormone mixture comprising insulin (10 micrograms/ml), hydrocortisone ($10^{-8}$ M), transferrin (5 micrograms/ml), glycyl-L-histidyl-L-lysine acetate (10 ng/ml), somatostatin (10 ng/ml) and TSH (10 mU/ml). Cells were grown in a 5 percent $CO_2$/95 percent air, humidified atmosphere at 37 degrees C. and were passaged bi-weekly with a split ratio of 1:10 using the CTC mixture.

In some instances the cells were passaged using trypsin rather than the CTC mixture. Cells were grown either to confluency or near confluency.

EXAMPLE 2

Seeding Of Cells

Prior to each assay, $1 \times 10^4$ to $1 \times 10^5$ cells were dispersed in each well of Costar (Data Packaging Corporation, Cambridge, Mass.) or Falcon (Becton Dickinson and Company Labware, Oxnard, Calif.) 12-well or 24-well plates. Cells were seeded in replicate fashion in the six hormone medium described in Example 1. Within 1 to 10 days prior to performing a specific assay, the six hormone medium was replaced with a five hormone medium, that is, one containing all of the same constituents as the six hormone medium except for thyrotropin.

Comparable seeding procedures were also performed in which the five hormone medium was replaced with Coon's modified F-12 medium containing 5 percent calf serum having no added hormones. Essentially similar results were produced.

EXAMPLE 3

Graves' Disease Immunoglobulin G Preparation (a) Serum was taken at the time of initial evaluation and on followup patient visits, where possible, and samples were stored at $-20$ degrees C. until the purification steps (described below) were performed. Purified IgGs were prepared from 1 to approximately 10 ml serum samples by double chromatography on DEAE-Sephadex using the Baumstark technique. The IgG was concentrated by ammonium sulfate precipitation, then solubilized and extensively dialyzed against 20 mM phosphate buffer, pH 7.2. Each IgG was terminally sterilized by passage through a Millipore 0.2 micron filter.

Comparable purifications were performed in which phosphate buffer was replaced with phosphate buffered saline solution pH 7 to 7.4 or the Hanks' Balanced Salt Solution. Essentially similar results were produced.

(b) In some instances, crude IgG preparations were prepared using a polyethylene glycol precipitation procedure: to 1 ml of serum was added 473 microliters of 50 percent polyethylene glycol (MW 3350; W/V in distilled water). After a 30 minute incubation period, tubes were centrifuged at $3,000 \times g$ for 10 minutes. The precipitate was washed with 1 ml of 15 percent polyethylene glycol and resuspended in 2 ml Hanks' Balanced Salt Solution. All procedures were performed at 4 degrees C.

EXAMPLE 4

Cyclic AMP Assay

Intracellular cAMP (a) The intracellular cAMP content of FRTL-5 thyroid cells was measured after growing cells in 24well Costar plates for 2 to 7 days and thereafter switching to the five hormone medium for a period of 10 days, as described in Example 2. The cells were then washed twice with HBSS before the addition of 75 microliters containing approximately 250 μg of IgG (purified as described in Example 3(a)), 85 microliters of HBSS+0.2 percent bovine serum albumin and 40 microliters of 2.5 mM IMX. Plates were incubated for 2 hours at 37 degrees C in a 5 percent $CO_2$/95 percent air humidified atmosphere. The reaction was terminated by medium aspiration, addition to the cells of 500 microliters of absolute ethanol and overnight incubation of the cells at $-20$ degrees C. After separation of the cell debris by centrifugation, aliquots of the ethanol supernatant solution were analyzed for cAMP using a Becton Dickinson radioimmunoassay kit. DNA levels were measured in the cell pellet; values were reported as picomoles cAMP/μg DNA. DNA levels between replicate wells were always within 5 percent.

Controls were run and non-specifc or basal values were measured in duplicate assays incubated in the presence of IMX media alone or containing normal IgG at the same concentration. The six hormone mixture was added as a positive control.

Extracellular cAMP (b) The extracellular cAMP content of FRTL-5 thyroid cells was measured in assays performed in the same manner described in Example 4(a) with the following exception. Aliquots of the medium removed by aspiration were analyzed for cAMP using a Becton Dickinson radioimmunoassay kit rather than aliquots of the ethanol supernatant solution. Substantially the same results were obtained.

EXAMPLE 5

Iodide Uptake Assay

FRTL-5 cells, grown as described in Example 1, were seeded and switched to the five hormone medium for a period of 10 days prior to performing the assay, as described in Example 2. Immediately prior to performing the assay, fresh media were added to the cells containing 0.005 mM IMX and GD IgG (approximately 2.5 mg). After 48 hours, culture medium was removed and cells were washed with 1 ml of modified HBSS with the following composition: 137 mM NaCl, 5.4 mM KCl, 1.3 mM $CaCl_2$, 0.4 mM $MgSO_4.7\ H_2O$, 0.5 mM $MgCl_2$, 0.4 mM $Na_2HPO_4.7\ H_2O$, 0.44 mM $KH_2\ PO_4$, 5.55 mM glucose, and 10 mM Hepes, pH 7.3. The assays were initiated by overlaying the cells with 500 microliters of the modified HBSS containing sufficient carrier-free $Na^{125}I$ and 10 uM NaI to give a specific activity for $^{125}I$ of 20 mCi/mmol. The reaction proceeded at 37 degrees C. in a humidified atmosphere and were terminated at 30 minutes by aspirating the radioactive medium, washing the cells with 1 ml of ice cold modified HBSS, treating them with 1 ml of 95 percent ethanol for 20 minutes, counting the material extracted with ethanol in a Beckmann 9000 gamma counter, and measuring the DNA content in the ethanol precipitated cell debris. Iodide uptake results are expressed as picomoles/ug DNA. Non-specific uptake was measured in duplicate assays incubated in the presence of IMX-media alone. (Comparable non-specific results were obtained in separate assays when normal human IgG at the same protein concentrations were substituted for the IMX-media.) The six hormone mixture was run as a positive control. Results were calculated on duplicate determinations.

EXAMPLE 6

Thymidine Incorporation (Growth Assay)

(a) [$^3$H]-Thydimine Incorporation: FRTL-5 thyroid cells plated in 12-well dishes were maintained in five hormone medium without TSH for 5 days, as described in Examples 1 and 2 above. The wells were washed once with HBSS before the addition microliters of purified GD IgG preparation (approximately 2.5 mg) and 2 microliters of [$^3$H]-thymidine (1.6×10$^6$ cpm). The plates were incubated for 72 hours at 37 degrees C. in 5 percent $CO_2$/95 percent air, humidified atmosphere. Thymidine uptake was terminated by a double wash with cold phosphate buffered saline (PBS), pH 7.2, and the addition of 1 ml of 5 percent aqueous trichloroacetic acid. After 10 minutes at 4 degrees C., the supernatant was aspirated, and 800 microliters of diphenylamine solution was added. This latter solution consisted of 5 g diphenylamine in 450 ml glacial acetic acid plus 10 ml sulfuric acid which in toto was mixed 20:8 (volume/volume) with water and with 0.1 volume 1 percent fresh acetaldehyde in water. After overnight development at room temperature, aliquots of each well were analyzed for DNA content by absorbence at 580 nm using spermine DNA standards and for [$^3$H]-thymidine content by radioactivity measurements in a liquid scintillation spectrometer. Hormones, normal IgG, or monoclonal antibodies were added as controls. Results were calculated on duplicate determinations.

(b) [$^{14}$C]-Thymidine Incorporation: Assays employing [$^{14}$C]-thymidine in place of [$^3$H]-thymidine were performed in the manner described in Example 6(a). Substantially the same results were obtained.

EXAMPLE 7

Clinical Determinations Employing Cyclic AMP Assay

The ability of IgG preparations, purified as described in Example 3(a) from the sera of 84 Graves' patients, to increase cAMP production was measured in cells deprived of TSH for 7 days and incubated for 3 hours with Graves' IgG (as described in Examples 2 and 4). Substantially the same results were obtained whether the intracellular cAMP assay (Example 4(a)) or the extracellular cAMP assay (Example 4(b)) was employed.

Figure 6:
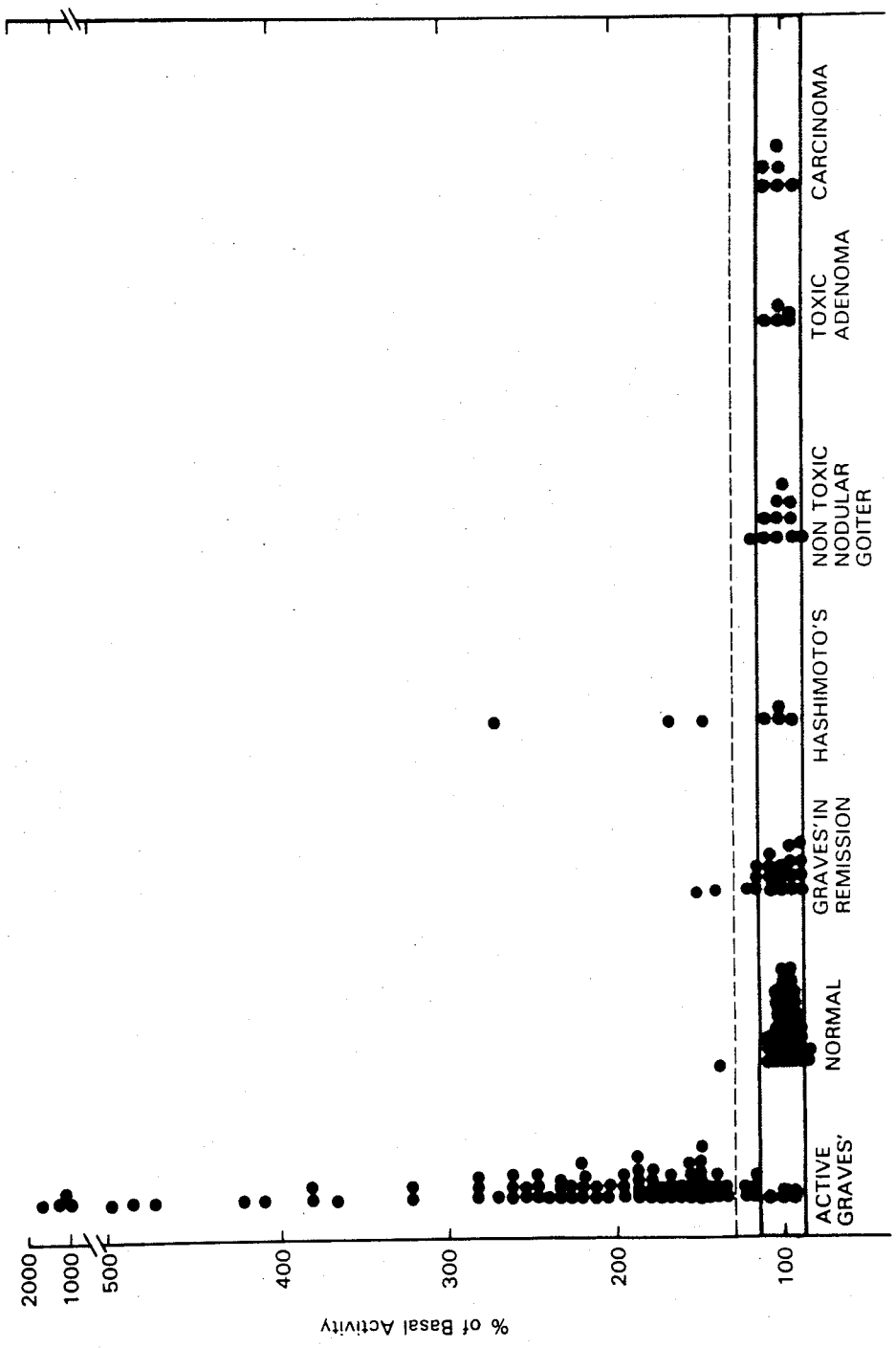
FIG. 6 graphically compares the ability of autoimmune IgGs from the sera of Graves' patients with active disease to increase cAMP levels in FRTL-5 cells greater than 2 SD (dashed line) above the values of a pool of IgGs from 10 normal individuals (shaded area) by comparison to IgGs from Graves' patients in remission and from patients with a thyroidal nontoxic nodular goiter, toxic adenoma, or carcinoma.

The magnitude of individual response using a single concentration of IgG between 250 and 500 micrograms/ml is presented in FIG. 6, column 1. The area between the horizontal solid lines represents the mean ±2 SD from over 100 independent assays using an IgG pool from 10 normal individuals. (The response of individual IgG preparations from 42 normal controls is presented in FIG. 6, column 2.)

The dashed line represents a value of 125 percent of basal activity; all IgG preparations having higher values were judged as positive based on the following criteria. First, IgG preparations with values greater than 125 percent exceeded the mean value of the IgG obtained from the pooled sera of 10 normal individuals by 2 standard deviations, and, with one exception, they exceeded the values of the 42 separate control IgG preparations tested. Excluding the one positive value, the mean value of the 41 normals was 97 percent of basal activity; the standard deviation was 6.3 percent; and the coefficient of variance was 0.065. The single positive serum IgG was not positive using non-optimal conditions, i.e., cells maintained in thyrotropin-free medium for only 1 day. Second, all IgG preparations tested at this single concentration exhibited a dose dependent increase in cAMP levels when 3 IgG concentrations were tested. IgG preparations from the 42 normal controls, with one exception noted, exhibited no dose dependent stimulatory action but rather exhibited a slight inhibitory activity at higher concentrations. Third, using the same reasoning, a similar value was used in studies employing human thyroid cell primary cultures.

Comparative tests were performed on IgG preparations from patients with other thyroid diseases. Three out of seven Hashimoto's cases exhibited a positive response but there were no positive responses detected in IgG preparations from eleven patients with non-toxic nodular goiter, four with toxic adenoma, and six with thyroid carcinoma (FIG. 6).

Of 21 Graves' patients in apparent clinical remission, only 2 were positive, based on the above criteria (FIG. 6, column 3), a striking difference from results in patients with active disease (FIG. 6, column 1).

Twenty of the 84 Graves' IgG preparations were tested on four separate occasions spanning 10 passages of the cells. These IgG preparations included two which were negative. Using conditions such as those described in Example 4 and expressing data as percent of basal, there was no change in results. All positive samples remained positive as a function of concentration. Further, values were replicated within ±5 percent for samples exhibiting stimulatory activity of 100 to 150 percent of basal. Samples with higher values above basal exhibited a slight interassay variation of ±5 percent to ±10 percent.

EXAMPLE 8

Clinical Determinations Employing Iodide Uptake Assay

IgG preparations obtained from the sera of 24 patients with Graves' disease, purified as described in Example 3(a), were assayed for cAMP elevations as described in Example 4 and iodide uptake by the assay described in Example 5, employing FRTL-5 rat thyroid cells prepared as described in Examples 1 and 2. All of the IgG preparations with positive values in the cAMP assay were also positive in the iodide uptake assay. Using these two assays and an FRTL-5 assay measuring thymidine uptake (Example 6), thyroid stimulating autoantibodies were found in 100 percent of patients with active Graves' disease and could broadly be grouped into three categories: IgG preparations with high stimulatory cAMP/iodide uptake activity but low to moderate effects on thymidine uptake; IgG preparations with moderate effects in all assays; and IgG preparations with low or undetectable cAMP/iodide stimulatory activity but high thymidine uptake activity.

The series of patients who were evaluated in the iodide uptake and cAMP assays were selected to include 9 individuals with active Graves' disease who did not have IgG preparations exhibiting positive values in the cAMP assay, 10 individuals with active Graves' disease whose IgG preparations were not only positive in the cAMP assay but spanned a wide range of values, and 5 patients whose Graves' disease was in remission.

Figure 7:
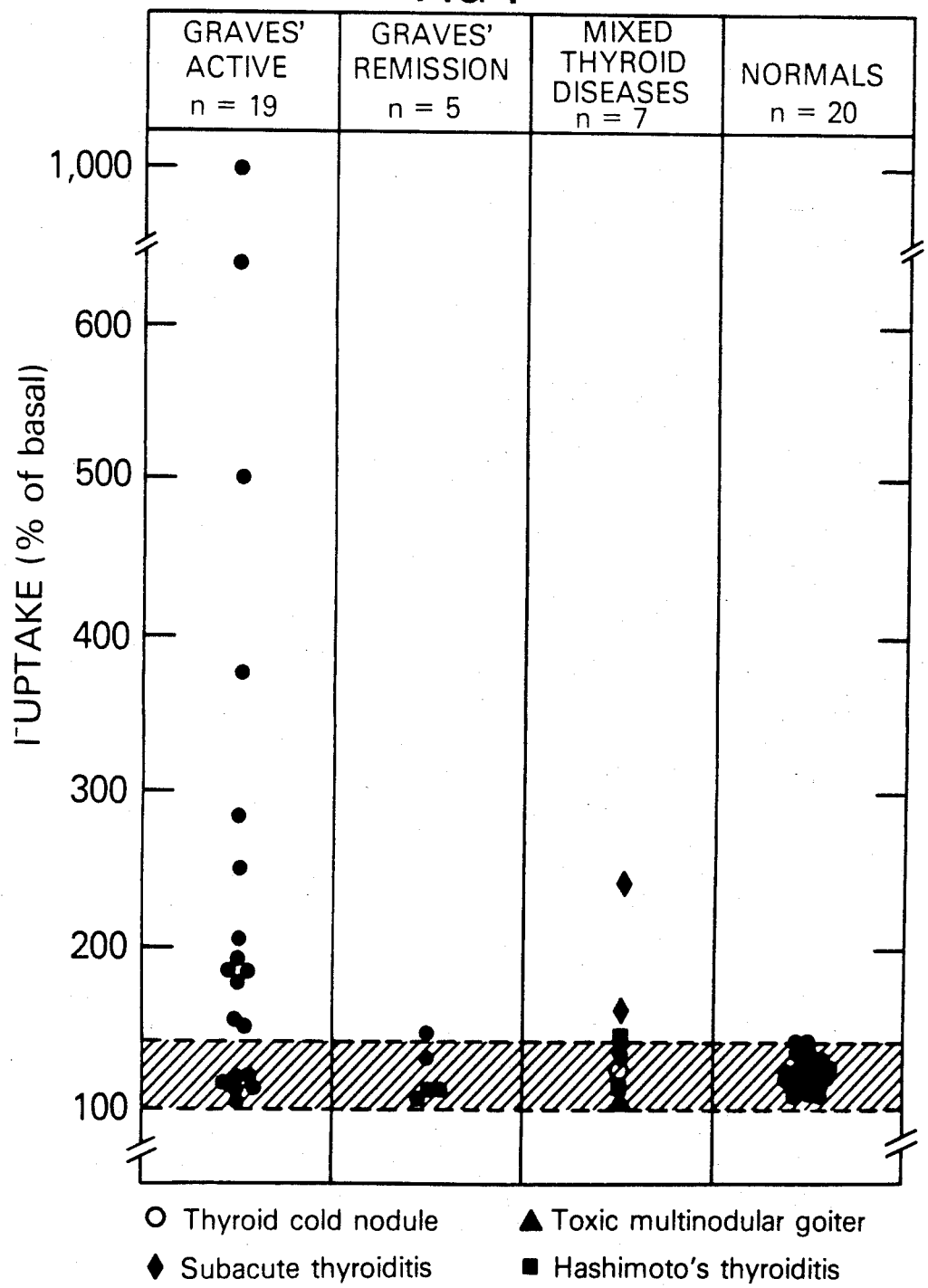
FIG. 7 graphically compares the ability of IgGs from a series of 19 patients with active Graves' disease to increase iodide uptake with IgGs from 20 normal individuals, from 5 patients with Graves' disease in remission and from 7 patients with other thyroid diseases.

The iodide uptake effected by IgG preparations obtained from 19 active Graves' patients and from 5 Graves' patients in remission are compared in FIG. 7 with data from 20 normal individuals. Results are expressed as percent of control incubations (five hormone medium without IgG). Using the mean normal IgG value ±2 SD, 119 percent ±20.8 percent of basal (N, the number of individuals tested, =20), IgG preparations from 13 of the 19 patients having active Graves' disease were considered positive in their ability to increase iodide uptake, i.e., those having values greater than 140 percent of control. IgG preparations from 4 of the 5 Graves' patients in remission had clearly negative responses and the fifth was weakly positive.

More revealing, however, is the comparative analysis between the results of I⁻ uptake and cAMP assays (Table II). All Graves' patients in remission exhibited values within normal limits in the cAMP assay.

TABLE II

Ability of Graves' IgG to Increase Iodide Uptake Compared with Their Ability to Increase cAMP Levels.

| Patient No. | Disease State* | cAMP % of basal | I Uptake % of basal | Thymidine Uptake % of basal |
|---|---|---|---|---|
| 1 | Rem | 100 | 100 | — |
| 2 | Rem | 100 | 114 | — |
| 3 | Rem | 100 | 145 | — |
| 4 | Rem | 118 | 108 | — |
| 5 | Rem | 123 | 130 | — |
| 6 | Act | 91 | 104 | 238 |
| 7 | Act | 94 | 107 | 509 |
| 8 | Act | 96 | 115 | 410 |
| 9 | Act | 96 | 186 | 171 |
| 10 | Act | 100 | 147 | 147 |
| 11 | Act | 106 | 113 | 151 |
| 12 | Act | 109 | 115 | 710 |
| 13 | Act | 112 | 250 | 155 |
| 14 | Act | 128 | 107 | 154 |
| 15 | Act | 138 | 189 | — |
| 16 | Act | 148 | 210 | — |
| 17 | Act | 153 | 150 | — |
| 18 | Act | 170 | 213 | — |
| 19 | Act | 171 | 178 | — |
| 20 | Act | 261 | 287 | — |
| 21 | Act | 369 | 700 | — |
| 22 | Act | 555 | 503 | — |
| 23 | Act | 1132 | 377 | — |
| 24 | Act | 2363 | 1000 | — |

*Rem = Remission
Act = Active

Figure 8:
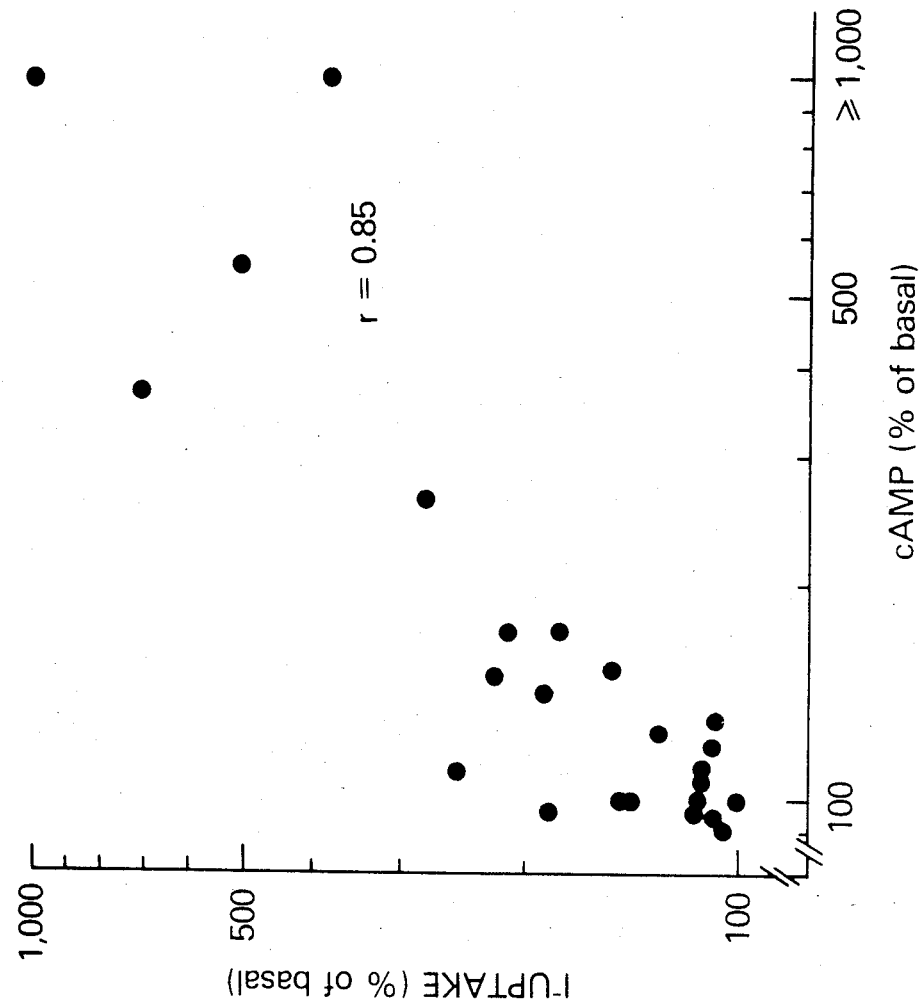
FIG. 8 graphically correlates the ability of an individual Graves' IgG to increase iodide uptake with its ability to increase cAMP levels in FRTL-5 thyroid cells which had been maintained in TSH-free medium for 10 days.

Although Graves' patients 6 to 14 were negative in the cAMP assay, 3 were positive in the iodide uptake assay (numbers 9, 10 and 13). Patients 15 to 24 were positive in both assays. A plot of the two assays, shown in FIG. 8, shows that there is a good correlation between the iodide uptake and cAMP assays, with an r value of 0.85.

These results indicate, based upon assays performed on patients in a clinical setting, that the iodide uptake assay can substitute for the cAMP assay and provide a measure of TSAb activity in Graves' patients.

EXAMPLE 9

Clinical Determinations Employing Labeled Thymidine Incorporation Assay

Figure 9:
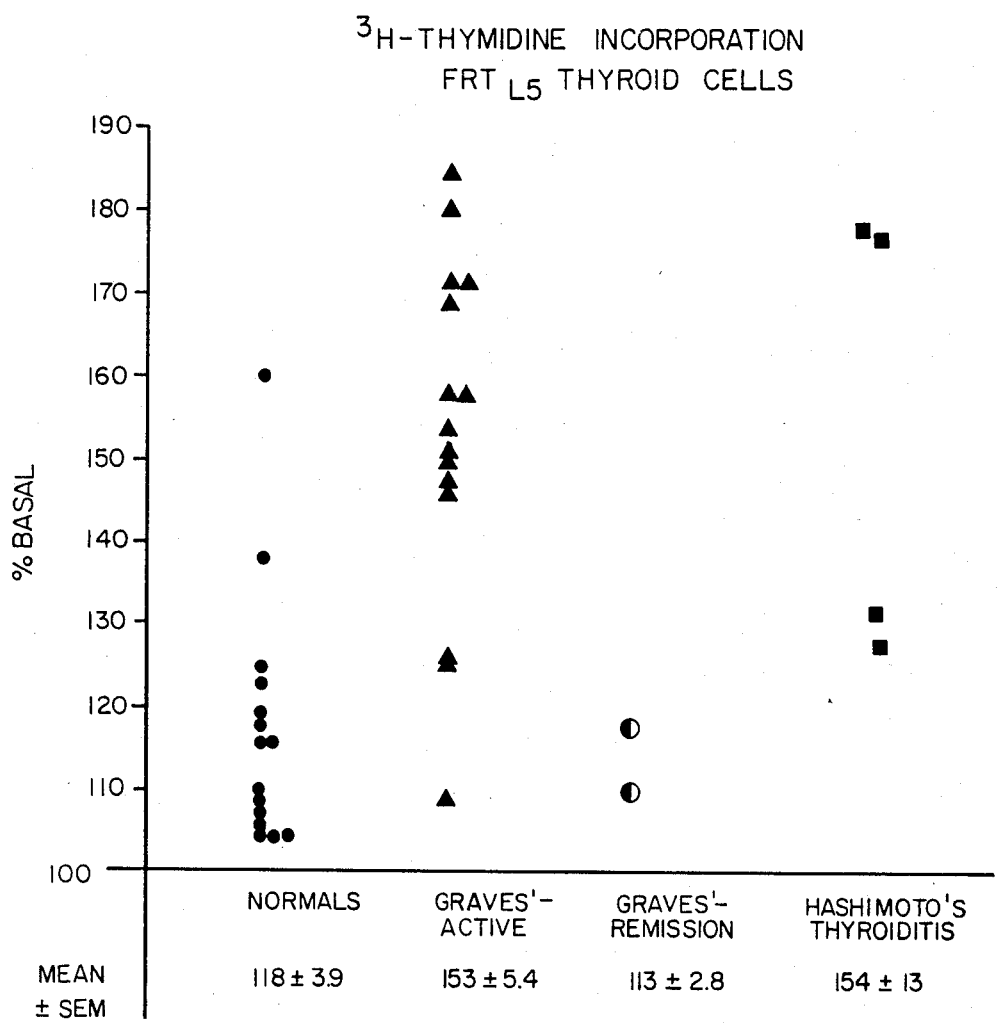
FIG. 9 graphically illustrates the ability of IgGs from patients with active Graves' disease to increase thymidine incorporation in FRTL-5 cells, expressed as percent of basal, by comparison to the ability of IgGs from normal individuals, from Graves' patients in remission, or from Hashimoto's thyroiditis, an autoimmune thyroid disease related to Graves' disease.

IgG preparations were obtained from the sera of individuals and purified as described in Example 3(a). Thymidine incorporation assays were performed as described in Example 6 employing FRTL-5 rat thyroid cells prepared as in Examples 1 and 2. IgG preparations from 15 normal individuals caused a mean augmentation of [$^3$H]-thymidine incorporation of 118±3.9 percent (mean ±SEM); the mean ±SEM of IgG preparations from 15 patients with active Graves' disease was found to be 153±5.4. Based on the mean ±SD (118±15) of the normal IgG preparations, values of thymidine uptake exceeding 140 percent of basal included IgG preparations from 12 (80 percent) of the 15 patients with active Graves' disease, from neither of the 2 patients with Graves' disease in remission, and from 2 of the 4 patients with Hashimoto's thyroiditis (FIG. 9). Based on the mean ±SD of the IgG preparations obtained from a pool of the 15 normal sera (110±7.2), 14 (93 percent) of the 15 patients with active Graves' disease were considered to have IgG preparations which significantly augmented [$^3$H]-thymidine incorporation, i.e., those with values greater than 120 percent of basal.

Figure 10:
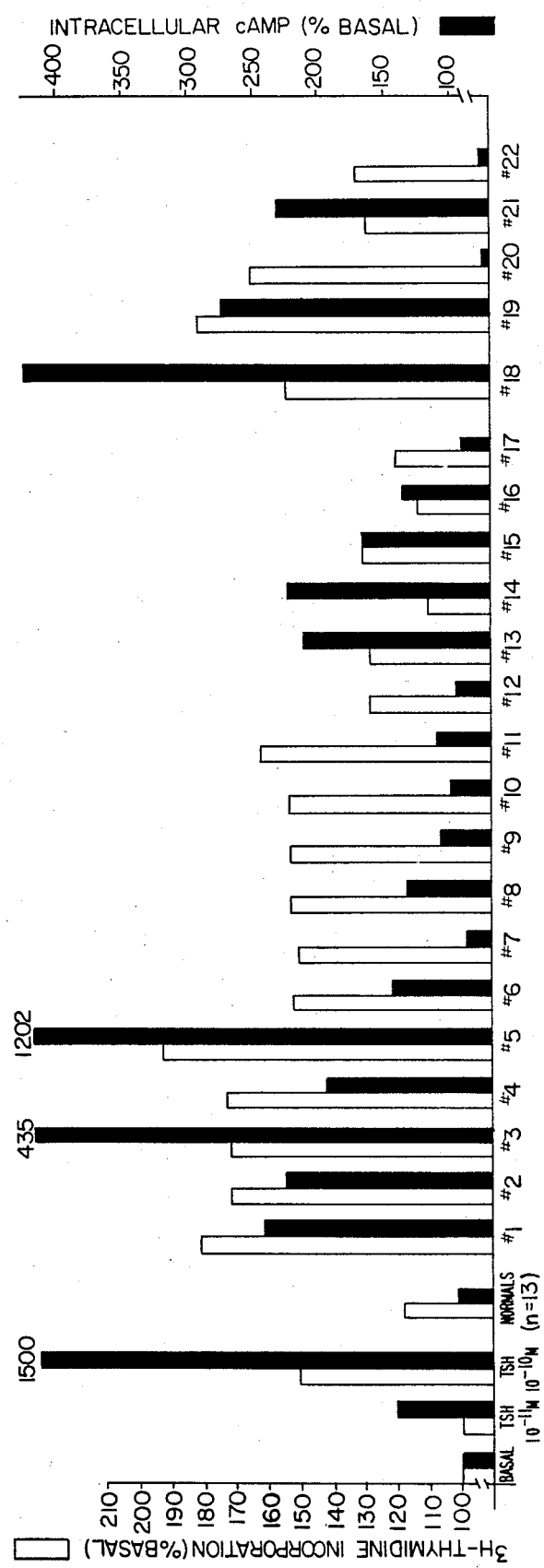
FIG. 10 graphically compares the ability of IgGs from individual patients with Graves' disease or with Hashimoto's disease to increase cAMP levels with their ability to increase thymidine incorporation in FRTL-5 thyroid cells.

In a second clinical evaluation, the IgG preparations of approximately 90 percent of patients with active Graves' disease were shown to stimulate cAMP production in FRTL-5 thyroid cells by comparison to normal IgG preparations (FIG. 6). The stimulatory effect of individual Graves' IgG preparations on thyroidal [$^3$H]-thymidine incorporation is compared to the effect on intracellular cyclic AMP production in FIG. 10; substantially the same results were obtained assaying extracellular cAMP production. It is evident that each patient's IgG preparation had a unique profile when results in both assays are compared. Thus, in the active Graves' patients (numbers 1 to 15), three broadly segregated groups may be categorized: patients whose IgG preparations exhibited coexistent potent cAMP and growth-promoting activity (numbers 1 to 5); patients whose IgG preparations exhibited a potent growth-promoting but low level of cAMP stimulatory action (numbers 6 to 12); and conversely, patients whose IgG preparations exhibited a potent cAMP stimulatory response but a low, growth-promoting activity (numbers 13 to 15). The two patients with Graves' disease in remission (numbers 16 and 17) had low levels of both IgG effects.

Patients with Hashimoto's thyroiditis likewise demonstrated a segregation of IgG effects with two individuals (numbers 20 and 22) possessing isolated potent growth-promoting IgG and two individuals (numbers 19 and 21) with coexistent cAMP activating and growth-promoting IgG.

Patient 18 was somewhat unique in that he suffered with myasthenia gravis and recurrent Graves' disease. The bi-potent IgG effector pattern was measured three months post $^{131}$iodine therapy.

Seven patients required sub-total thyroidectomy (numbers 2, 3, 4, 8, 9, 10 and 11) and five required $^{131}$iodine therapy (numbers 5, 6, 7, 12 and 19) for control of their Graves' disease. These individuals had persistent thyrotoxicosis after a 12 to 18 month course of thionamide therapy and all demonstrated significant levels of growth-promoting IgG. Three Graves' patients who required surgery (numbers 7, 10 and 11) had IgG preparations which increased [$^3$H]-thymidine incorporation but did not stimulate cAMP production (FIG. 10), whereas no patient with low levels of growth-promoting activity but an active cAMP stimulatory IgG preparation was found in the surgical group.

EXAMPLE 10

Detection Of Thyroid Inhibitory Factors By FRTL-5 Thyroid Cell Assays

Figure 11:
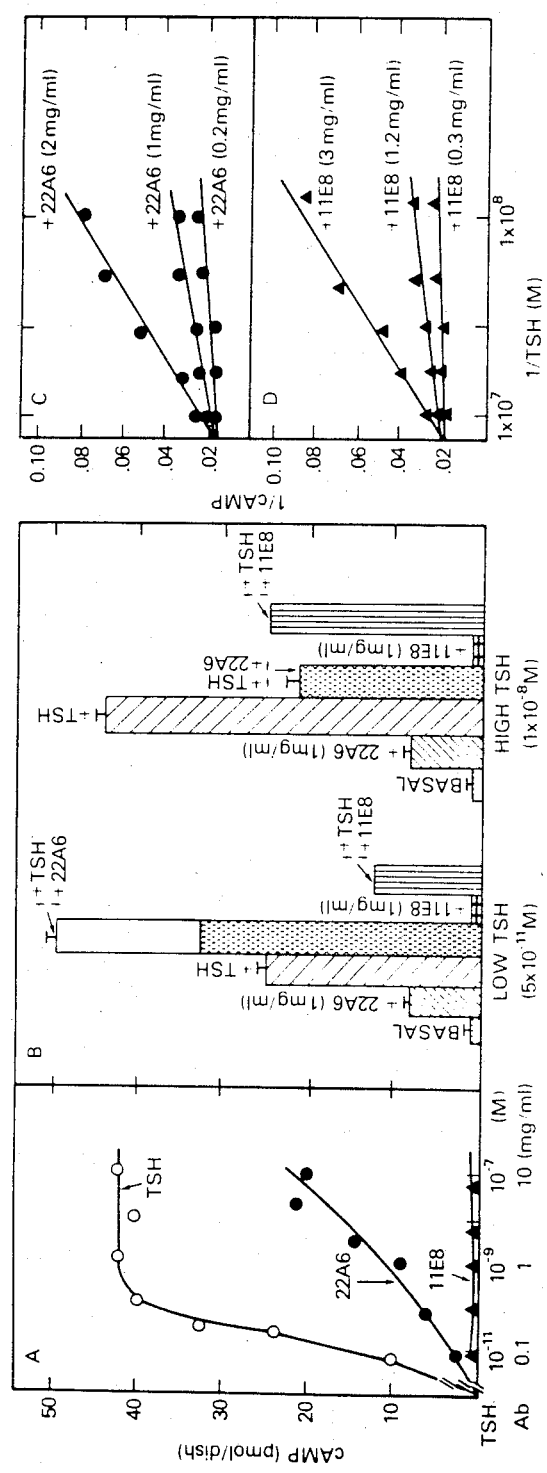
FIG. 11A graphically illustrates the ability of monoclonal antibodies 11E8 or 22A6 to elevate cAMP levels in FRTL-5 cells in comparison to the effect of TSH, the FRTL-5 cells having been maintained in TSH-free medium for 10 days.
FIG. 11B graphically compares the ability of monoclonal antibodies 11E8 or 22A6 to perturb cAMP levels in FRTL-5 cells (identically maintained as in FIG. 11A) when incubated together with low or high concentrations of TSH.
FIGS. 11C and 11D graphically illustrate, respectively, the ability of monoclonal antibodies 11E8 or 22A6 to competitively prevent TSH induced increases in cAMP levels as measured by double reciprocal plots of the cAMP level versus different high concentrations of TSH.

Experiments were carried out to test the effect of monoclonal antibodies (designated 22A6 and 11E8) on cAMP levels of FRTL-5 functioning rat thyroid cells in continuous culture by comparison to TSH using FRTL-5 cells which had been grown in five hormone (without TSH) media 7 days before the experiment was initiated. The data presented in FIG. 11 illustrates the versatility of assaying such monoclonal antibodies employing the cAMP assay in the presence of low ($5 \times 10^{-11}$ M) or high ($1 \times 10^{-8}$ M) concentrations of TSH, that is, a greater range of conclusions can be drawn. Double-reciprocal plots of the ability of antibodies 22A6 or 11E8 (at the noted concentrations) to inhibit the TSH-stimulated enhancement of cAMP-levels in FRTL-5 cells can be used to evaluate mechanism. In this case, such plots establish these antibodies as anti-TSH receptor antibodies since they competitively perturb function.

The 22A6 monclonal stimulating antibody causes concentration dependent increases in cAMP levels in rat FRTL-5 thyroid cells (FIG. 11A). At low concentrations of TSH, the antibody enhances the ability of TSH to increase cAMP levels in these same cells in a more than additive manner, i.e., 22A6 is an agonist, whereas at high concentrations of TSH it is an apparent inhibitor, i.e., an antagonist (FIG. 11B). In contrast to the 22A6 antibody, the monoclonal antibody designated 11E8 does not increase cAMP levels in rat FRTL-5 thyroid cells (FIG. 11A) and exhibits only inhibitory activity with respect to TSH (FIG. 11B). Both antibody 22A6 (FIG. 11C) and antibody 11E8 (FIG. 11D) indicated competitive inhibition of TSH stimulated cAMP levels in the rat thyroid cells when tested at high TSH concentrations. These data are consistent with the conclusion that both antibodies are directed at the TSH receptor; these results are also compatible with data which indicated both of these monoclonal antibodies to be directed at different determinants of the TSH receptor.

The ability of the antibody 11E8 to inhibit TSH activity cannot be accounted for by the presence in the 11E8 preparation of a contaminating anti-TSH activity. This is unlikely given (i) the competitive (as opposed to the uncompetitive or mixed) inhibition data in FIG. 11 as well as (ii) results which show that, although 11E8 is made by using bovine thyroid membrane preparations, it is bioactive when human TSH is used and (iii) 11E8 has no anti-TSH activity in radioimmunoassays.

Since antibodies 11E8 and 22A6 are both anti-TSH receptor antibodies which are representative of individual species of IgG preparations in Graves' patients, it is evident that the FRTL-5 assay systems may be used to measure inhibitory as well as stimulatory activity.

Industrial Applicability

The FRTL-5 continuous rat thyroid cell strain employed in the present invention comprises rapidly growing cells which maintain all normal thyroid cell functions, including iodide uptake and thyroglobulin synthesis, over prolonged periods of culture. These cells have a thyrotropin responsive adenylate cyclase and an absolute growth requirement for thyrotropin. These characteristics make the FRTL-5 strain of thyroid cells ideally suited to performing the assays of the present invention, which assays may be used to determine and quantify thyroid stimulatory and inhibitory factors. Specifically, these factors may be evaluated by assays measuring thymidine incorporation, cAMP elevation and iodide uptake. Each of these assays individually provides information which is at least as reliable as assay methods used heretofore and a combination of the thymidine incorporation assay and at least one of the cAMP assay or the iodide uptake assay is capable of providing 100 percent positive tests of thyroid stimulatory or inhibitory factors. The clinical predictive value of these assays is particularly useful with patients suffering from Graves' and related autoimmune thyroid diseases in that it provides a convenient means of evaluating the long term efficacy of drug therapy, such as thionamide therapy and/or the need for surgical or radioiodine therapy.

I claim:

1. A process for preparing a continuous, functional rat cell strain, having the identifying characteristics of FRTL-5 ATCC CRL 8305 cell strain, comprising:
   culturing a continuous, functional rat cell line FRTL in a medium comprising thyrotropin and calf serum to obtain FRTL-5 cells and cloning said FRTL-5 cells to obtain cells of an FRTL-5 strain having the identifying characteristics of FRTL-5 ATCC CRL 8305 cell strain.

2. The process for preparing a continuous, functional rat cell strain, FRTL-5, according to claim 1 wherein said medium is Coon's modified Ham's F-12 medium.

3. The process for preparing a continuous, functional rat cell strain, FRTL-5, according to claim 1 wherein said medium is supplemented with a mixture of hormones.

4. The process for preparing a continuous, functional rat cell strain, FRTL-5, according to claim 3 wherein said mixture of hormones comprises insulin, hydrocortisone, transferrin, glycyl-L-histidyl-L-lysine acetate, and somatostatin.

5. The process for preparing a continuous, functional rat cell strain, FRTL-5 according to claim 1 wherein the cell line is cultured in vitro.

6. The process for preparing a continuous, functional rat cell strain, FRTL-5, according to claim 1 wherein said calf serum is present in the range of about 2.5 to 15 percent, by volume, based on the volume of the medium.

7. The process for preparing a continuous, functional rat cell strain, FRTL-5, according to claim 6 wherein said calf serum is present in an amount of about 5 percent, by volume, based on the volume of the medium.

8. The process for preparing a continuous, functional rat cell strain FRTL-5 according to claim 1 wherein FRTL-5 cells are cloned to obtain an FRTL-5 ATCC CRL 8305 cell strain.

9. A continuous, functional rat thyroid cell strain, FRTL-5, having the accession number ATCC CRL 8305.

10. A continuous, functional rat thyroid cell strain having the identifying characteristics of FRTL-5 ATCC CRL 8305 cell strain.